United States Patent [19]

Pálosi et al.

[11] Patent Number: 4,916,149
[45] Date of Patent: Apr. 10, 1990

[54] DIURETIC AND SALURETIC 4-CHLORO-3-SULFAMOYLBENZOIC ACID HYDRAZIDES

[75] Inventors: Endre Pálosi; Dezsö Korbonits, both of Budapest; Erzsébet Molnár née Bakó, Szödliget; Ida Szoboda née Kanzel, Dunakeszi; Lásló Hársing, Budapest; György Simon, Budapest; Sándor Virág, Budapest; Vera Gergely, Budapest; Katalin Marmarosi née Kellner, Biatorbágy, all of Hungary

[73] Assignee: Chinoin Gyogyszer es Vegyeszeti Termekek Gyara Rt., Budapest, Hungary

[21] Appl. No.: 295,925

[22] Filed: Dec. 29, 1988

[30] Foreign Application Priority Data

Dec. 30, 1987 [HU] Hungary .............................. 6131/87

[51] Int. Cl.[4] .................. A61K 31/415; C07D 235/22; C07D 235/28
[52] U.S. Cl. ..................................... 514/387; 514/395; 548/305; 548/329
[58] Field of Search ................ 548/305, 329; 514/387, 514/395

[56] References Cited

U.S. PATENT DOCUMENTS 3,767,643 10/1973 Kunstmann et al. ............... 548/305

Primary Examiner—Richard A. Schwartz
Attorney, Agent, or Firm—Herbert Dubno; Jonathan Myers

[57] ABSTRACT

The present invention relates to novel compounds of the general formula

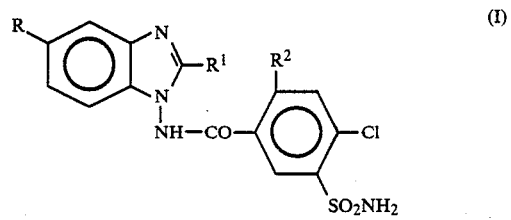

wherein

R is hydrogen atom or a trifluoromethyl, carboxy, $C_{2-5}$alkoxycarbonyl, cyano, benzoyl, sulfamoyl or $C_{1-4}$alkylsulfonyl group;

$R^1$ is hydrogen atom or a linear or branched chain $C_{1-4}$alkyl, $C_{1-4}$alkylthio, $C_{1-4}$alkylsulfonyl, benzylthio, benzylsulfonyl, phenyl, hydroxy or mercapto group; and $R^2$ is hydrogen or chlorine atom, as well as their pharmaceutically acceptable salts.

The compounds according to the invention possess diuretic and saluretic activity with an advantageous Na/K ratio.

4 Claims, 2 Drawing Sheets

DIURETIC AND SALURETIC 4-CHLORO-3-SULFAMOYLBENZOIC ACID HYDRAZIDES

FIELD OF THE INVENTION

The invention relates to novel benzimidazole derivatives of the formula

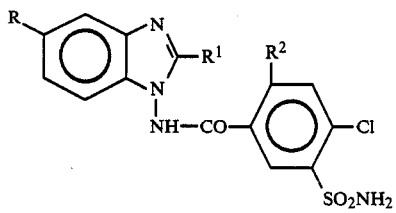

wherein
R is hydrogen atom or a trifluoromethyl, carboxy, $C_{2-5}$alkoxycarbonyl, cyano, benzoyl, sulfamoyl or $C_{1-4}$alkylsulfonyl group;
$R^1$ is hydrogen atom of a a linear or branched chain $C_{1-4}$alkyl, $C_{1-4}$alkylthio, $C_{1-4}$alkylsulfonyl, benzylthio, benzylsulfonyl, phenyl, hydroxy or mercapto group; and
$R^2$ is hydrogen or chlorine, as well as their pharmaceutically acceptable salts and pharmaceutical compositions containing these compounds.

The compounds of the formula (I) possess diuretic and saluretic activity.

BACKGROUND OF THE INVENTION

Diuretics of the chlorobenzenesulfonamide type containing a free carboxy group on the benzene ring (DE-OS Nos. 1,122,541 and 2,247,828), carboxylic acid amide group (DE-OS No. 1,158,927) or carboxylic acid hydrazide group (Hungarian Pat. Nos. 150,352 and 152,300) have earlier been described. Thus, Furosemide from the first group (DE-PS No. 1,122,541; and K. Sturm, et al.: Chem. Ber. 99, 328 (1966)), Diapamide from the second group (L. T. Blouin et al.: J. New Drugs 3, 302 (1963)) and Clopamide from the third group (E. Jucker et al.: Arzneim.-Forsch. 13, 269 (1963)/have all become well-known drugs.

The chemical structure of the compounds according to the present invention significantly differs from those of the known diuretics mentioned above.

Benzimidazole type derivatives having diuretic effect have been described in U.S. Pat. No. 4,420,487; however, these compounds do not contain a benzoic acid hydrazide moiety and thus their structure is significantly different from that of the compounds according to the invention.

DESCRIPTION OF THE INVENTION

Figure 1:
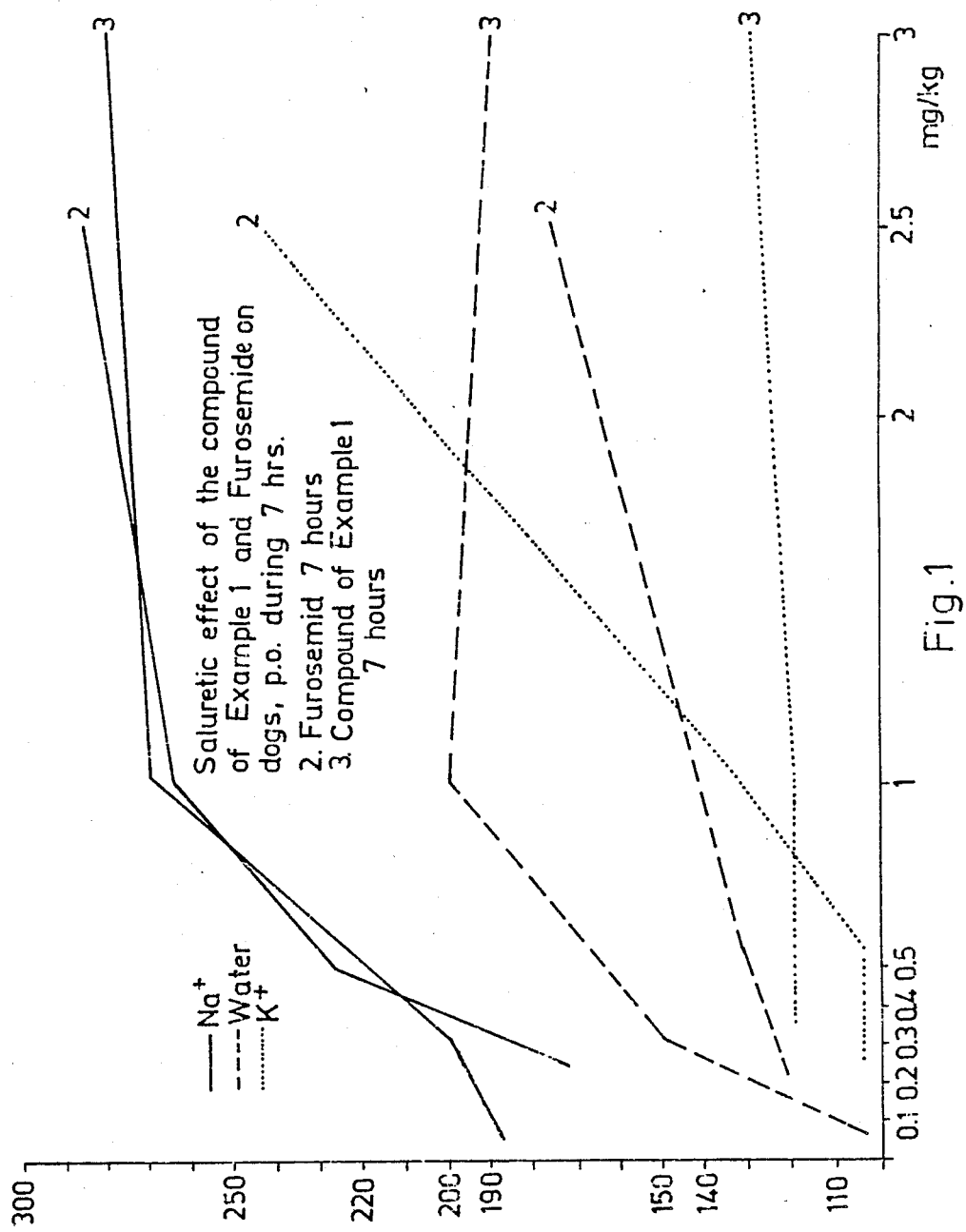
FIGS. 1 and 2 show the correlation of the diuretic dose to the water, sodium and potassium discharging effect.

The compounds of the present invention were compared with Dihydrochlorothiazide and Furosemide in rats by administration of a 5 mg/kg oral screen dose. The compound prepared according to Example 1 proved to be particularly advantageous concerning the discharged urine volume as well as ion diuresis and had a highly preferable Na/K index.

It is particularly advantageous that, in addition to their excellent efficiency, the therapeutic safety of the compounds according to the invention is better than that of the "high-ceiling" substances since the onset and course of the diuresis and saluresis are not too rapid and violent. Their effect lasts 24 hours following administration.

In comparison to the reference drugs, another advantage of the compound described in Example 1 is that it does not induce any deterioration of the glucose tolerance even in a high dose (30 mg/kg) and has no significant effect on the uric acid concentration or the cholesterol level of the serum.

The acute toxicity of the compounds according to the invention is substantially lower than those of the reference drugs used for comparison thus, their therapeutic safety indexes are highly better.

The antihypertensive activity of the compounds was tested in spontaneously hypertensive (SH) male rats by using a dose of 5 mg/kg. A hypotension of 21.1% was induced by the compound of Example 1 by 12 hours after administration. Furosemide, used as reference drug, induced a similar hypotension in a dose of 100 mg/kg.

For oral use in the human therapy tablets, dragées or capsules containing 1 to 200 mg of the active ingredient together with the usual carriers and excipients can be used; for intravenous administration injectable aqueous solutions containing the active ingredient in the form of a water-soluble salt such as alkaline metal salts, e.g. the sodium salt may be used.

According to another aspect of the invention, there is provided a process for the preparation of the new compounds of the formula (I),
wherein
R is hydrogen atom or a trifluoromethyl, carboxy, $C_{2-5}$alkoxycarbonyl, cyano, benzoyl, sulfamoyl or $C_{1-4}$alkylsulfonyl group;
$R^1$ is hydrogen atom or a linear or branched chain $C_{1-4}$alkyl, $C_{1-4}$alkylthio, $C_{1-4}$alkylsulfonyl, benzylthio, benzylsulfonyl, phenyl, hydroxy or mercapto group; and
$R^2$ is hydrogen or chlorine,
as well as their pharmaceutically acceptable salts, which comprises
(a) reacting a 1-aminobenzimidazole derivative of the formula

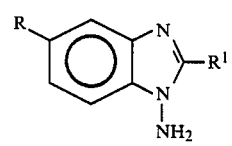

wherein
R and $R^1$ are the same as defined above,
with a carboxylic acid derivative of the formula

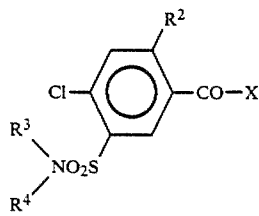

(III)

wherein
X is chlorine or a hydroxy, —OCH$_2$CN, methoxy, ethoxy, —OCOOCH$_3$ or —OCOOC$_2$H$_5$ group;
$R^2$ is the same as defined above; and
$R^3$ and $R^4$ are hydrogen or
$R^3$ and $R^4$ together form a =CHN(CH$_3$)$_2$ group, and
when a compound of the formula

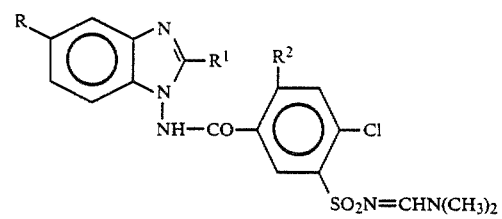

(Ia)

wherein
R, $R^1$ and $R^2$ are the same as defined above is obtained, removing the protecting group in an alkaline medium,
or
 (b) reacting a 2-aminophenylhydrazine derivative of the formula

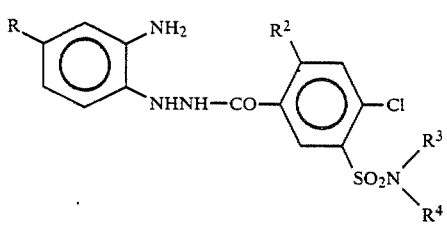

(IVb)

wherein
R, $R^2$, $R^3$ and $R^4$ are the same as defined above, with carbon disulfide, potassium ethyl xanthate or thiophosgene and additionally, when a compound of the formula

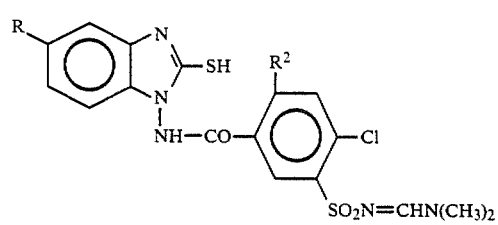

(Ib)

wherein
R, $R^1$ and $R^2$ are the same as defined above is obtained, removing the protecting group in an alkaline medium to obtain a compound of the formula

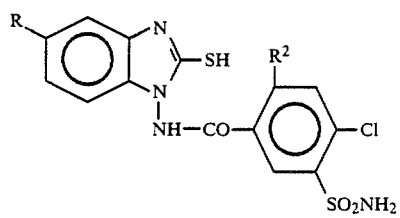

(Ie)

wherein
R and $R^2$ are the same as defined above, which represent a more confined group of the compounds of the formula (I);
or
 (c) reacting a 2-aminophenylhydrazine derivative of the formula

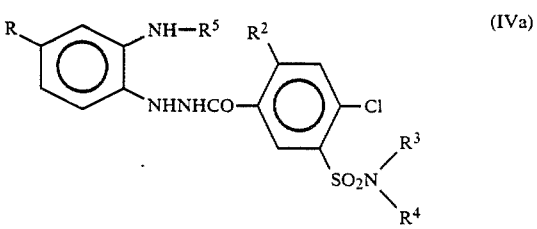

(IVa)

wherein
R, $R^2$, $R^3$ and $R^4$ are the same as defined above; and
$R^5$ is hydrogen atom or an acetyl, propionyl, butyryl, isobutyryl, pentanoyl, 2-methylbutyryl, trimethylacetyl or benzoyl group,
with formic or acetic acid and additionally, when a compound of the formula (Ia) is obtained, removing the protecting group, in an alkaline medium, to obtain compounds of the formula (I),
wherein
R and $R^2$ are the same as defined above; and
$R^1$ is hydrogen or methyl, ethyl, propyl, isopropyl, butyl, isobutyl, tertiary butyl or phenyl group;
or
 (d) reacting a 2-aminophenylhydrazine derivative of the formula (IVb),
wherein
R, $R^2$, $R^3$ and $R^4$ are the same as defined above, with an N,N$^1$-dicarboalkoxy-S-methylisothiourea derivative of the formula

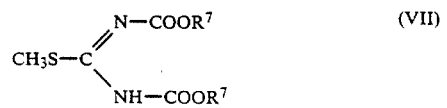

(VII)

wherein
$R^7$ is a C$_{1-4}$alkyl group and additionally, when a compound of the formula

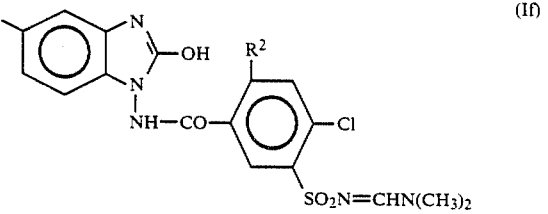

(If)

wherein
R and $R^2$ are the same as defined above is obtained, removing the protecting group in an alkaline medium to obtain compound of the formula

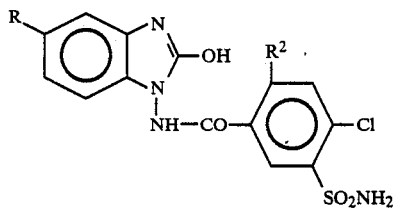

(Id)

wherein
R and $R^2$ are the same as defined above, which represent a more confined group of the compounds of the formula (I);
or (e) reacting a compound of the formula (Ib) or (Ie), wherein
R, $R^2$, $R^3$ and $R^4$ are the same as defined above, with an alkylating agent and additionally, when a compound of the formula

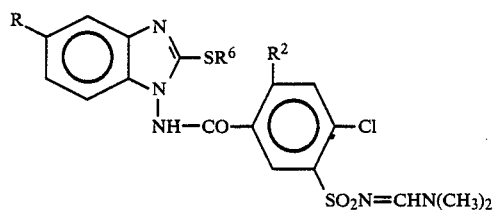

(Ih)

wherein
R and $R^2$ are the same as defined above; and
$R^6$ stands for a linear or branched chain $C_{1-4}$alkyl or benzyl group is obtained, removing the protective group in an alkaline medium, to prepare compounds of the formula

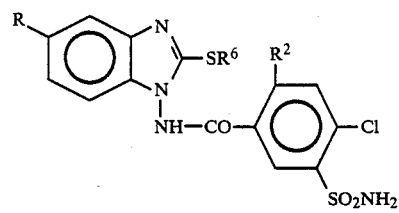

(Ic)

wherein
R, $R^2$ and $R^6$ are the same as defined above, which represent a more confined group of the compounds of the formula (I);
or (f) reacting a 2-benzimidazolyl thioether derivative of the formula (Ic) or (Ih),
wherein
R, $R^2$, $R^3$, $R^4$ and $R^6$ are the same as defined above, with an oxidizing agent and additionally, when a compound of the formula

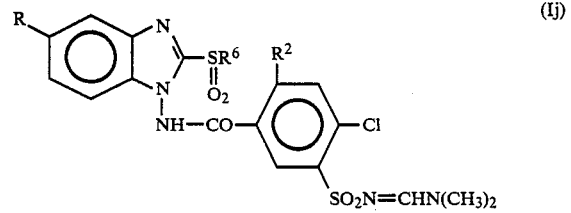

(Ij)

wherein
R, $R^2$ and $R^6$ are the same as defined above is obtained, removing the protecting group, in an alkaline medium to obtain compounds of the formula

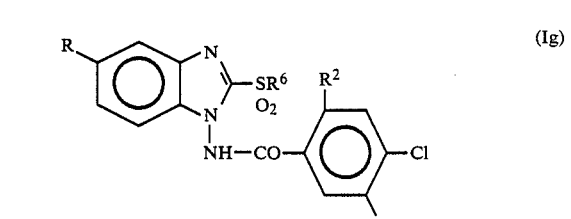

(Ig)

wherein
R, $R^2$ and $R^6$ are the same as defined above, which represent a more confined group of the compounds of the formula (I)
and, if desired, converting the compounds of the formula (I) obtained by using any of the above processes (a) to (f) to their pharmaceutically acceptable salts.

The compounds of the formulae (Id) and (Ie) may be present in the tautomeric forms illustrated in FIGS. H and K, respectively.

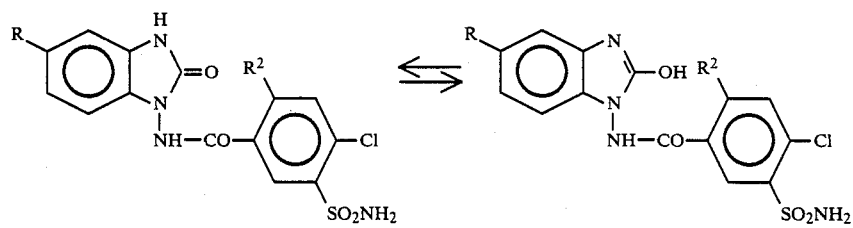

FIG. H

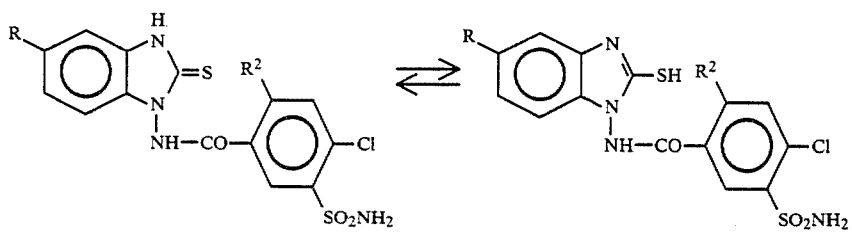

FIG. K

In the process (a) of the invention a 1-aminobenzimidazole derivative of the formula (II) is reacted with a carboxylic acid derivative of the general formula (III) to give a compound of the formula (I) as illustrated in the Reaction Scheme (A).

Reaction Scheme (A)

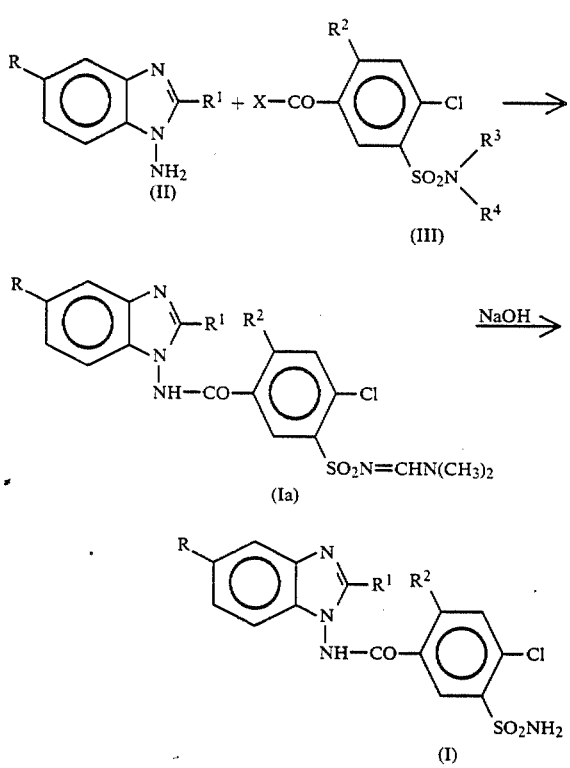

In this reaction, the free carboxylic acid or a reactive derivative thereof, e.g. an acyl halide or a lower alkyl or active ester of the acid or a mixed anhydride are used for the acylation. Most suitable alkyl esters are the methyl and ethyl ester whereas cyanomethyl ester may be used as an active ester. The reactants are employed in equimolar amounts. Triethylamine or sodium amide is added to the reaction mixture.

It is suitable to substitute the sulfonamide group in some cases. For this purpose a condensation with formamide acetals proved to be very useful to give aminomethylidenesulfonamides as shown in Reaciton Scheme (B).

Reaction Scheme (B)

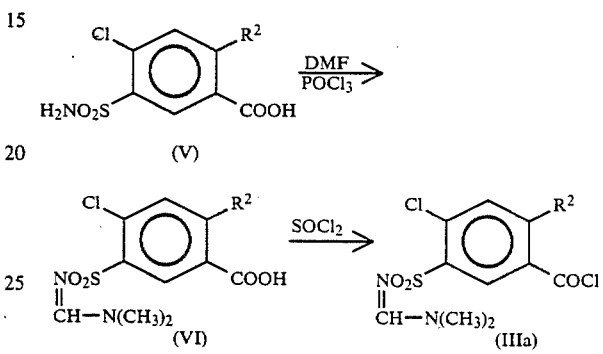

This reaction may particularly be useful when, according to Reaction Scheme (A), acyl chlorides are used for the acylation since these "protected" acyl chlorides are much more stable than those containing a free sulfonamide group. The reaction with dimethylformamide dimethylacetal may be carried out in dimethylformamide at a temperature between 40° C. and 80° C. The compounds of the formula (VI) may most preferably be prepared in such a way that the dimethylformamide dimethylacetal is prepared in situ in the reaction mixture to obtain immediately the acid of formula (VI) containing the "protected" sulfonamido group which in turn can be reacted with thionyl chloride to give the acyl chlorides of the formula (IIIa) in a high yield.

The acylation by acyl chlorides or mixed anhydrides is accomplished in a polar solvent such as tetrahydrofuran, dioxane, pyridine, dimethylformamide, dimethylacetamide or dimethylurea. The temperature of this reaction may be varied between $-20°$ C. and the boiling point of the solvent used. When the reaction is carried out in a non-basic solvent, then an organic base, e.g. triethylamine or dimethylaniline is added as an acid binding agent.

When the acylation is carried out by using acyl chlorides of the formula (IIIA), then the reaction may be carried out in a mixture of water and a water-miscible organic solvent, in the presence of a carbonate or bicarbonate of an alkaline metal or alkaline earth metal as acid binding agent.

The water-miscible organic solvents may be protic or aprotic. Ether-type solvents (e.g. dioxane, tetrahidrofuran), ketones (e.g. acetone) or acid amides (e.g. dimethylformamide or dimethylacetamide) may be used as aprotic solvents. As protic solvents lower aliphatic alcohols (e.g. methanol, ethanol, propanols) may be used which are completely miscible with water.

As alkaline metal carbonates sodium or potassium carbonate, as alkaline earth metal carbonates magnesium or calcium carbonate and as alkaline metal bicarbonate, sodium or potassium bicarbonate may be used.

The reaction is preferably carried out at a temperature between 0° C. and 100° C., particularly preferably between 10° C. and 30° C.

For preparing the mixed anhydride, an acid of the formula (VI) is reacted with an alkyl chloroformate, mainly with methyl or ethyl chloroformate. The mixed anhydride may be separated or preferably prepared in the reaction mixture and reacted with the amino compound of the formula (II) without isolation.

For the removal of the protective group, alkaline hydrolysis is employed. This reaction is carried out in an aqueous medium by using strong inorganic bases, suitably sodium or potassium hydroxide at a temperature range of 20° C. to 80° C., preferably 50° C. to 60° C. The inorganic base is used in an amount of 2 to 6 moles, preferably 3 to 4 moles as calculated for 1 mole of the compound to be hydrolyzed.

When using a carboxylic acid (X=OH) as acylating agent, the reaction is accomplished in the presence of a condensating agent. Dicyclohexylcarbodiimide or tetrachlorosilane are most convenient for this purpose. This reaction is preferably carried out in pyridine.

In the process (b) of the invention, a 2-aminophenylhydrazine derivative of the formula (IVb) is reacted with carbond disulfide, potassium ethyl xanthate or thiophosgene to give a benzimidazole derivative of the formula (Ie) according to the Reaction Scheme (C).

Reaction Scheme (C)

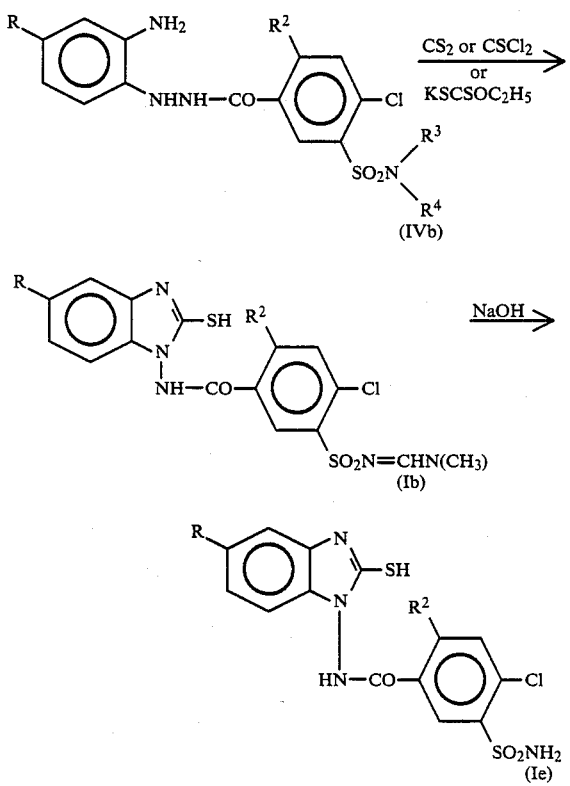

According to an embodiment of this process variant, a compound of the formula (IVb) is reacted with carbon disulfide at a temperature between 10° C. and 150° C., preferably between 30° C. and 100° C., in the presence of a base in water or in an organic solvent.

Alcohols such as methanol, ethanol or a propanol may be used as organic solvent. Tertiary amines, e.g. triethylamine or pyridine, preferably alkaline metal hydroxides, most preferably potassium hydroxide may be used as bases.

According to an other embodiment of the process variant (b), a compound of the formula (IVb) is brought into reaction with an alkaline metal ethyl xanthate, preferably with potassium ethyl xanthate a at a temperature range from 20° C. to 150° C., preferably between 50° C. and 100° C. in water or in an organic solvent.

Alcohols such as methanol, ethanol or propanols are suitable organic solvents though tertiary amines such as triethylamine or pyridine may also be used as solvents.

According to a further embodiment of the process variant (b), a compound of the formula (IVb) is reacted with thiophosgene in the presence of a base in water or in an organic solvent at a temperature between 0° C. and 120° C., preferably between 20° C. and 100° C.

For this reaction organic solvents may be used which are inert to the reactants. Suitable solvents are ethers such as dioxane or tetrahydrofurane. Tertiary amines, e.g. triethylamine or pyridine or preferably alkaline metal hydroxides such as sodium or potassium hydroxide may be used as bases.

For the removal of the protective group from the compounds of the formula (Ib), alkaline hydrolysis is employed under the conditions defined for process (a).

In the process (c) of the invention, a 2-aminophenylhydrazine derivative of the formula (IVa) is heated with formic or acetic acid to obtain a compound of the formula (I) as shown in the Reaction Scheme (D).

Reaction Scheme (D)

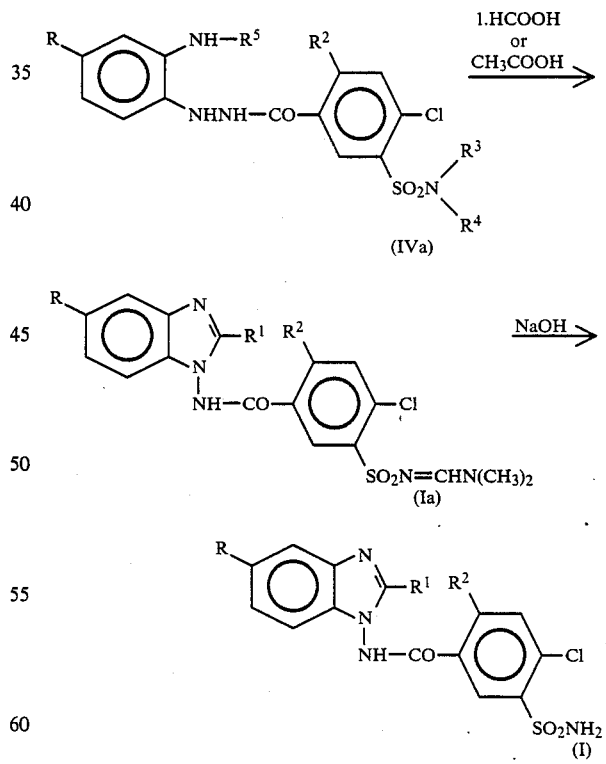

In this reaction, the formic or acetic acid, respectively serves also as solvent. This reaction is accomplished at a temperature between 50° C. and the boiling point of the acid used, preferably between 80° C. and 100° C. when the meaning of $R^3$ and $R^4$ is different from hydrogen, then the protective group is removed by alkaline hydrolysis under the conditions defined for the process (a) above.

In the process (d) of the invention, a 2-aminophenylhydrazine derivative of the formula (IVb) is transformed to a benzimidazole derivative of the formula (Id) by using an equimolar amount of N,N¹-dicarboalkoxy-S-methylisothiourea as illustrated in the Reaction Scheme (E).

Reaction Scheme (E)

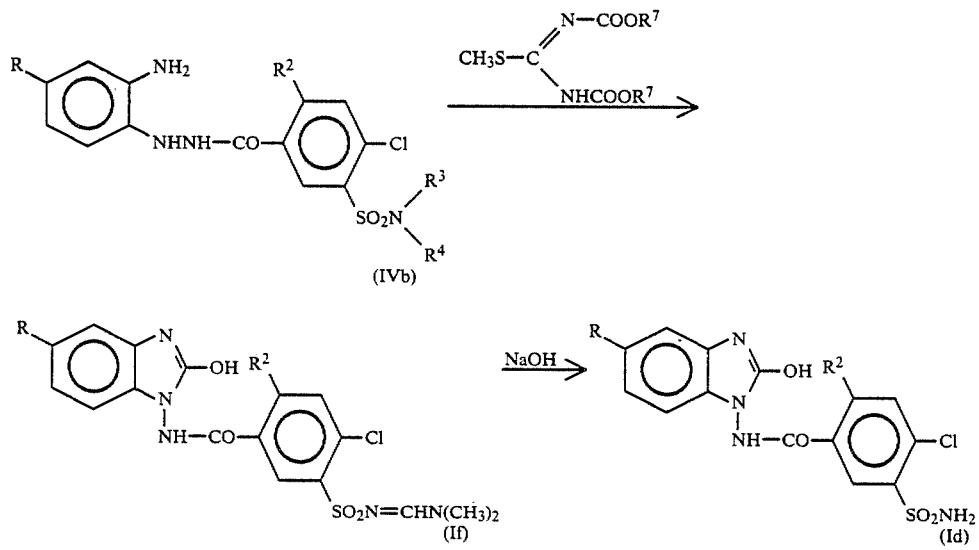

This reaction is accomplished in a polar organic solvent at a temperature between 50° C. and the boiling point of the organic solvent used. Suitable solvents are pyridine, ethylene glycol or dimethylsulfoxide; preferably, dimethylformamide or dimethylacetamide are used.

In the case of the compounds of formula (If), the protective group is removed by alkaline hydrolysis under conditions defined above for the process (a).

In the process (e) of the invention, a substance of the formula (Ib) or (Ie) is reacted with an alkylating agent in a known manner to give a compound of the formula (Ic) as presented in the Reaction Scheme (F).

Reaction Scheme (F)

Suitable alkylating agents are alkyl sulfates, alkyl halides or alkyl p-toluenesulfonates in water or in an organic solvent. As alkyl sulfates methyl or ethyl sulfate, as alkyl halides methyl, ethyl, propyl, butyl or benzyl chloride, bromide or iodide and as alkyl p-toluenesulfonates methyl, ethyl, propyl and benzyl esters are mainly used. Lower alcohols such as methanol or ethanol may be employed as organic solvents.

This reaction is accomplished in the presence of a base. Alkaline metal hydroxides, preferably sodium or potassium hydroxide as well as alkaline metal alkoxides, preferably sodium methoxide or ethoxide may be taken in consideration as bases.

According to a preferred embodiment of the reaction, the compound of the formula (Ib) is dissolved in the solution of an equivalent amount of sodium hydroxide in water or in the solution of an equivalent amount of sodium ethoxide in ethanol and the alkylating agent is added to the above solution.

The alkylation is carried out at a temperature between 20° C. and the boiling point of the solvent used.

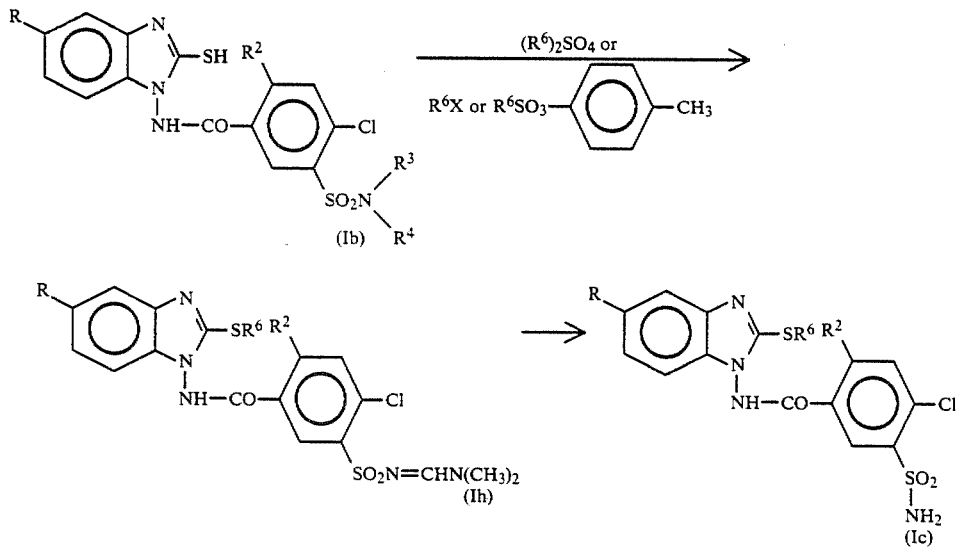

For removing the protective group from the compounds of the formula (Ih), alkaline hydrolysis is used under the conditions defined above for process (a).

In the process (f) of the invention, a 2-benzimidazolyl thioether derivative of the formula (Ic) or (Ih) is oxidized in a known manner to a compound of the formula (Ig) as shown in the Reaction Scheme (G).

Reaction Scheme (G)

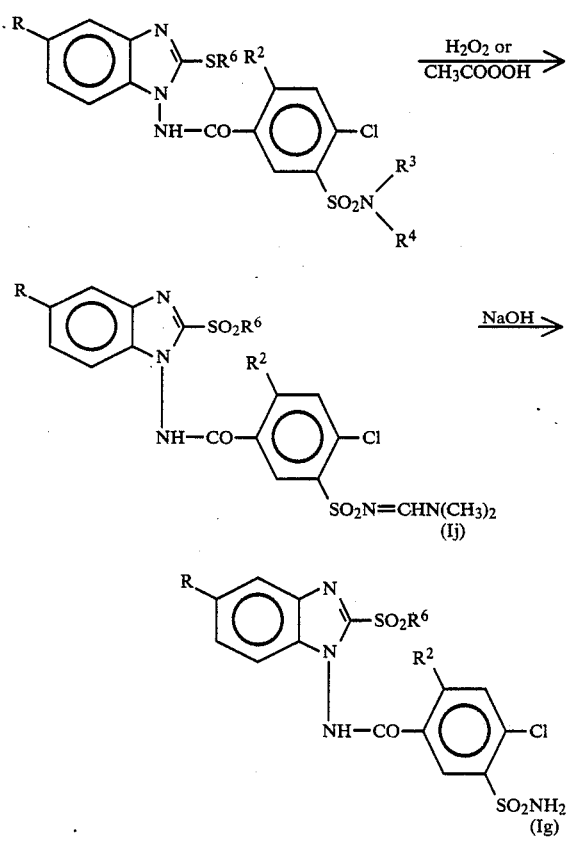

Hydrogen peroxide or peroxyacetic acid may be used as oxidizing agent for this purpose. The reaction may be carried out in water or in an organic solvent or in the mixture of water with an organic solvent. Formic or acetic acid may suitably be employed as organic solvents. The reaction may be accomplished between 20° C. and 120° C., preferably between 60° C. and 100° C.

Alkaline hydrolysis under the conditions defined above for process (a) may be used to remove the protective group from the compounds of the formula (Ij).

The compounds of the formula (I) containing a carboxy group as R are particularly useful for therapeutic purposes since these substances are capable to form stable alkaline metal salts which are well soluble in water at a neutral pH value. Among these, sodium and potassium salts are mainly useful though calcium and magnesium salts can also be taken in consideration for specific purposes.

Experiments carried out in rats and dogs show that the compounds according to the invention have an excellent saluretic activity appearing by 1 to 2 hours after administration, reaching a maximum between the 3rd and 5th hour and lasting for 24 hours whereby a prolonged and mild diuresis is ensured. A particular advantage of the new compounds appears in their preferable sodium/potassium index and their low effect on the serum cholesterol level. The compounds of the invention are particularly useful for intravenous administration.

For intravenous administration in the human therapy, aqueous injectable solutions containing as active ingredient 0.1 to 100 mg of an alkaline metal salt of a compound according to the invention are used. For oral use tablets, dragées or capsules containing 1 to 300 mg of active ingredient together with pharmaceutical carriers and/or other excipients can be taken in consideration.

The invention is illustrated in detail by the following non-limiting Examples.

EXAMPLE 1

105 ml of carbon disulfide were added to a suspension containing 100 g of 2-amino-4-methoxycarbonyl-N-(4'-chloro-3'-sulfamoylbenzoyl)phenylhydrazine in 400 ml of methanol, then potassium hydroxide dissolved in 190 ml abs. ethanol was added dropwise to the reaction mixture at a temperature below 20° C. under stirring and cooling by cold water. After the addition, the mixture was refluxed while stirring for 2 hours, then the clear brown solution was allowed to stand overnight. Next day 145 ml of acetic acid were added to the solution, which was stirred for 1 hour, then evaporated to its half volume. The residue was poured into 1500 ml of water while stirring. The beige precipitate was filtered by suction, washed with water and dried. The crude product was dissolved while boiling in a mixture of dimethylformamide and water (1:1), the hot solution was clarified by activated carbon and filtered as hot. After cooling down, the crystalline beige precipitate was filtered by suction, washed with water and dried at 100° C. under reduced pressure to give 75 g (68%) of 1-(4'-chloro-3'-sulfamoylbenzoyl)amino-5-methoxycarbonylbenzimidazole-2-thione, m.p.: 242°–245° C. (with decomposition).

After recrystallization from a mixture of dimethylformamide and water (1:2) it melted at 258°–261° C. (with decomposition).

Analysis (%) for $C_{16}H_{13}ClN_4O_5S_2$:

| calculated: | C 43.59; | H 2.97; | N 12.71; | Cl 8.04; | S 14.55 |
|---|---|---|---|---|---|
| found: | C 43.80; | H 2.78; | N 12.57; | Cl 8.62; | S 14.60 |

48.4 g of the ester obtained as described above were stirred with 330 ml of 2N sodium hydroxide solution at 50° C. for 4 hours. The clear yellow solution was cooled down and acidified to pH 3 to 4 by adding 2N hydrochloric acid. The precipitate was filtered by suction, washed with water and dried at 80° C. The crude product obtained was recrystallized from a mixture of dimethylformamide and water (1:1) under clarifying by activated carbon. Thus, 1-(4'-chloro-3'-sulfamoylbenzoyl)amino-5-carboxybenzimidazole-2-thione containing 1 molecule of dimethylformamide was obtained in the form of snow-white tiny crystals.

This product containing dimethylformamide was boiled with 430 ml of distilled water for 30 minutes. After cooling down, the white crystals were filtered by suction, washed with water and dried at 80° C. under reduced pressure to give 37.4 g (76.5%) of 1-(4'-chloro-3'-sulfamoylbenzoyl)amino-5-carboxybenzimidazole-2-thione monohydrate, as snow-white crystals, m.p.: 320°–322° C.

Analysis (%) for $C_{15}H_{11}ClN_4O_5S_2.H_2O$:

| calculated: | C 40.50; | H 2.94; | N 12.59; | Cl 7.97; | S 14.41; |
|---|---|---|---|---|---|
| found: | C 40.22; | H 2.80; | N 12.20; | Cl 7.70; | S 14.65. |

Preparation of the starting material (A) 80 ml of hydrazine hydrate were poured into the suspension of 172.5 g of methyl 4-chloro-3-nitrobenzoate in 1600 ml of abs. ethanol under stirring, then the reaction mixture was refluxed while stirring for 45 minutes. The starting material dissolved and the product started to precipitate. After cooling down, the product was filtered by suction, washed with abs. ethanol and water successively until it became free from chloride ion. Thus, 4-methoxycarbonyl-2-nitrophenylhydrazine (143.6 g, 85%) was obtained as yellow crystals m.p.: 169°–171° C.

Analysis (%) for $C_8H_9N_3O_4$:

| calculated: | C 45.49; | H 4.29; | N 19.89; |
|---|---|---|---|
| found: | C 45.58; | H 4.31; | N 20.33. |

(B) 127 g of 4-chloro-3-sulfamoylbenzoyl chloride (prepared as described in: J. Med. Chem. 11, 970 (1968)) dissolved in 500 ml of dioxane were added to suspension of 105 g of phenylhydrazine derivative obtained above under (A) in 1 liter of dioxane under stirring, then 26.5 g of anhydrous sodium carbonate were added to the mixture which was then stirred under a reflux condenser in a hot water bath for 5 hours. After cooling down, it was filtered and the filtrate was evaporated under reduced pressure to give a gum as a residue which was stirred wtih 1500 ml of water until it became powder, then it was filtered by suction, washed with water and dried at 80° C. to give 203 g (94.7%) of 4-methoxycarbonyl-2-nitro-N-(4'-chloro-3'-sulfamoylbenzoyl)-phenylhydrazine as yellow powder, m.p.: 144°–147° C.

Analysis (%) for $C_{15}H_{13}ClN_4O_7S$:

| calculated: | C 42.01; | H 3.05; | N 13.07; | Cl 8.27; | S 7.48; |
|---|---|---|---|---|---|
| found: | C 41.71; | H 3.38; | N 13.06; | Cl 8.01; | S 7.86. |

(C) 10 g of Raney nickel catalyst were added to a solution containing 60 g of the nitro compound obtained above under (B) in 500 ml of methoxyetanol (ethylene glycol monomethyl ether) maintained at 70° C., then the mixture was hydrogenated at 70° C. under a pressure of 10 atmospheres in a shaker. After ceasing of the hydrogen uptake, the reaction mixture was cooled down and the catalyst was filtered off. The filtrate was evaporated under reduced pressure and the gum residue was stirred with 500 ml of water until it disaggregated to a filterable powder. The product was filtered by suction, washed with water and dried at 80° C. to yield 51 g (91%) of 2-amino-4-methoxycarbonyl-N-(4'-chloro-3'-sulfamoylbenzoyl)phenylhydrazine as a beige powder, m.p.: 214°–215° C. (with decomposition).

Analysis (%) for $C_{15}H_{15}ClN_4O_5S$:

| calculated: | C 45.17; | H 3.79; | H 14.05; | Cl 8.89; | S 8.04; |
|---|---|---|---|---|---|
| found: | C 45.72; | H 3.71; | N 13.75; | Cl 9.29; | S 7.94. |

EXAMPLE 2

42 ml of carbon disulfide were poured to a suspension of 38.5 g of 2-amino-4-carboxy-N-(4'-chloro-3'-sulfamoylbenzoyl)phenylhydrazine in 160 ml of methanol then 20.72 g of potassium hydroxide dissolved in 105 ml of abs. ethanol was added dropwise to the above mixture while stirring. The solution obtained was boiled for 1 hour, then cooled down and the pH value was adjusted between 4 and 5 by adding 2N hydrochloric acid. The precipitate was filtered by suction, washed with water and dried at 80° C. to afford 31.8 g (75%) of 1-(4'-chloro-3'-sulfamoylbenzoyl)amino-5-carboxybenzimidazole-2-thione as a beige powder, m.p.: 290°–295° C. (with decomposition). After purifying as described in Example 1, the product proved to be identical with that of Example 1.

Preparation of the starting material (A) 25.7 g of 4-methoxycarbonyl-2-nitro-N-(4'-chloro-3'-sulfamoylbenzoyl)phenylhydrazine were stirred with 120 ml of 2N sodium hydroxide solution at 50° C. for 4 hours. After cooling down, the pH value of the dark violet solution was adjusted to 5 by adding 2N hydrochloric acid. The yellow precipitate was filtered by suction, washed with water and dried at 80° C. to give 23 g (92.5%) of 4-carboxy-2-nitro-N-(4'-chloro-3'-sulfamoyl-benzoyl)phenylhydrazine as a yellow powder, m.p.: 273°–275° C. (with decomposition).

Analysis (%) for $C_{14}H_{11}ClN_4O_7S$:

| calculated: | C 40.53; | H 2.67; | N 13.50; | Cl 8.50; | S 7.70; |
|---|---|---|---|---|---|
| found: | C 40.23; | H 2.88; | N 13.76; | Cl 8.54; | S 7.66. |

(B) 4 g of 10% palladium-on-carbon catalyst were added to a suspension of 41.4 g of the nitro compound prepared above in Example 2(A) in 500 ml of 96% ethanol then the reaction mixture was heated to 60° to 70° C. under stirring and 150 ml of 30% aqueous sodium hypophosphite solution were added dropwise to at such a rate that violent foaming was avoided. After cooling down, it was filtered and the filter cake was stirred with 70 ml of 2N sodium hydroxide solution. The catalyst was filtered off and the pH value of the filtrate was adjusted to 5 by adding 2N hydrochloric acid. The precipitate was filtered by suction, washed with water and dried at 80° C. to give 32 g (83%) of 2-amino-4-carboxy-N-(4'-chloro-3'-sulfamoylbenzoyl)phenylhydrazine, m.p.: 240°–244° C. (with decomposition).

After recrystallization from a mixture of dimethylformamide and water (1:2) this product melted at 245°–246° C. (with decomposition).

Analysis (%) for $C_{14}H_{13}ClN_4O_5S$:

| calculated: | C 43.70; | H 3.40; | N 14.56; | Cl 9.21; | S 8.33; |
|---|---|---|---|---|---|
| found: | C 43.83; | H 3.40; | N 14.21; | Cl 8.94; | S 8.10. |

EXAMPLE 3

A mixture containing 8 g of 2-amino-4-methoxycarbonyl-N-(4'-chloro-3'-sulfamoylbenzoyl)phenyl-hydrazine and 3.2 g of potassium ethyl xanthate in 30 ml of pyridine was refluxed for 30 minutes, then pyridine was evaporated under reduced pressure. After dissolving the residue in 40 ml of glacial acetic acid the solution was poured into 160 ml of water. The precipitate was filtered by suction, washed with water and dried at 80° C. to give 8.2 g (93%) of 1-(4'-chloro-3'-sulfamoylbenzoyl)amino-5-methoxycarbonylbenzimidazole-2-thione as a pink powder, m.p.: 258°–261° C. (with decomposition) after recrystallization from a mixture of dimethylformamide and water (1:2).

EXAMPLE 4

0.85 ml of thiophosgene was dropped into a solution containing 4 g of 2-amino-4-methoxycarbonyl-N-(4'-chloro-3'-sulfamoylbenzoyl)phenylhydrazine in 22 ml of 1N sodium hydroxide solution while stirring and cooling with cold water. The mixture was stirred at room temperature for 4 hours, then refluxed for 30 minutes. After cooling down, the pH value of the mixture was adjusted to 7 by the addition of 1N sodium bicarbonate solution then, after stirring for 30 minutes, the pH was adjusted to 5 by acetic acid. The precipitate was filtered by suction, washed with water and dried at 80° C. to give 4.35 g (98.5%) of 1-(4'-chloro-3'-sulfamoylbenzoyl)amino-5-methoxycarbonylbenzimidazole-2-thione, as a beige powder, m.p.: 258°–261° C. (with decomposition) after recrystallization from a mixture of dimethylformamide and water (1:2).

EXAMPLE 5

2.54 g of 4-chloro-3-sulfamoylbenzoyl chloride were added in little portions to the solution of 2.2 g of 1-amino-5-methoxycarbonylbenzimidazole-2-thione in 8 ml of dimethylformamide and 1.4 ml of triethylamine while stirring. The reaction mixture was set aside overnight, then the pH value was adjusted to 5 by acetic acid and it was diluted with 100 ml of water. The separated gum slowly disaggregated to a powder which was filtered by suction, washed with water and dried at 80° C. The crude product obtained was boiled with 10 ml of glacial acetic acid for 30 minutes, then poured into 50 ml of water. The separated gum disaggregated to a powder by stirring. The precipitate was filtered by suction, washed with water and dried at 80° C. to give 2.4 g (54.5%) of 1-(4'-chloro-3'-sulfamoylbenzoyl)amino-5-methoxycarbonylbenzimidazole-2-thione, as a beige powder, m.p.: 258°–261° C. (with decomposition) after recrystallization from a mixture of dimethylformamide and water (1:2).

Preparation of the starting material (A) After boiling 105.6 g of 4-methoxycarbonyl-2-nitrophenylhydrazine with 1 liter of glacial acetic acid for 1 hour, the clear orange-red solution was evaporated under reduced pressure. The residue was stirred with 1500 ml of water, the crystalline precipitate was filtered by suction, washed with water and dried at 80° C. to give 123 g (97%) of 4-methoxycarbonyl-2-nitro-N-acetylphenylhydrazine, in the form of yellow powder-like crystals, m.p.: 182°–185° C., which melted at 190°–192° C. after recrystallization from aqueous ethanol.

Analysis (%) for $C_{10}H_{11}N_3O_5$:

| calculated: | C 47.43; | H 4.38; | N 16.59; |
| found: | C 47.55; | H 4.73; | N 16.58. |

(B) 107.7 g of the benzoic acid derivative prepared above in Example 5(A) were refluxed with 425 ml of 1N sodium hydroxide solution for 10 minutes, then the solution was filtered to give a clear dark red solution which was acidified to a pH value of 3 to 4 by adding acetic acid. The crystalline precipitate was filtered by suction, washed with water and dried at 80° C. to obtain 98 g (96.4%) of 4-carboxy-2-nitro-N-acetylphenylhydrazine, as a yellow crystalline solid, m.p.: 262°–263° C. The melting point was raised to 272°–274° C. (with decomposition) after recrystallization from 50% aqueous ethanol.

(C) The solution of 116.3 g of the nitro compound prepared above in Example 5(B) in 490 ml of 1N sodium bicarbonate solution was filtered to give a clear solution which was then hydrogenated in the presence of 10 g of 10% palladium-on-carbon catalyst until the hydrogen uptake ceased. After filtering off the catalyst, the filtrate was acidified to pH 4 by adding 5N hydrochloric acid. The crystalline precipitate was filtered by suction, washed with water and dried at 80° C. to yield 80.9 g (79.6%) 2-amino-4-carboxy-N-acetylphenylhydrazine in the form of beige crystalline solid, m.p.: 145°–150° C. (with decomposition). After recrystallization from abs. ethanol the m.p. was raised to 156°–158° C. (with decomposition).

Analysis (%) for $C_9H_{11}N_3O_3$:

| calculated: | C 51.67; | H 5.30; | N 20.09; |
| found: | C 51.31; | H 5.49; | N 19.79. |

(D) 62.75 g of the amine compound prepared above in Example 5(C) were dissolved in a solution of 36 g of potassium hydroxide in 450 ml of abs. ethanol then 20.5 ml of carbon disulfide was added and the mixture was refluxed under stirring for 5 hours. A yellow crystalline solid was precipitated. 250 ml of hot water were added to the mixture, the solution obtained was clarified by activated carbon, filtered and about 200 ml of ethanol are distilled off from the filtrate under reduced pressure. To the remaining solution 65 ml of acetic acid was added, the yellow crystalline precipitate was filtered by suction, washed with water and dried at 80° C. to yield 46 g (61%) 1-acetylamino-5-carboxybenzimidazole-2-thione, as a white crystalline solid, m.p.: 334°–338° C. after recrystallization from 50% aqueous ethanol.

Analysis (%) for $C_{10}H_9N_3O_3S$:

| calculated: | C 48.00; | H 3.61; | N 16.72; | S 12.76; |
| found: | C 48.70; | H 3.50; | N 16.70; | S 12.74. |

(E) 25.1 g of the benzimidazole derivative prepared according Example 5(D) were refluxed with 100 ml of 2N hydrochloric acid under stirring for 6 hours. After cooling down, the crystals were filtered by suction, washed with water and dried at 80° C. to yield 20.5 g (98%) 1-amino-5-carboxybenzimidazole-2-thione, as a beige crystalline solid, m.p.: 301°–304° C. (with decomposition).

Analysis (%) for $C_8H_7NO_2S$:

| calculated: | C 45.92; | H 3.37; | N 20.08; | S 15.30; |
| found: | C 45.40; | H 3.34; | N 19.92; | S 15.70. |

(F) A suspension containing 20.5 g of the carboxylic acid prepared according to Example 5(E) in 250 ml of methanol was saturated by gaseous hydrogen chloride an then refluxed under stirring for 30 minutes while slowly introducing gaseous hydrogen chloride. After cooling down, the crystals were filtered by suction and added as wet to 80 ml of 1N sodium bicarbonate solution under vigorous stirring. After stirring for 30 minutes, the crystalline precipitate was filtered by suction, washed with water and dried at 80° C. Thus, 19.9 g, (91%) 1-amino-5-methoxycarbonylbenzimidazole-2-thione was obtained in the form of bone-coloured crystals, m.p.: 239° C. (with decomposition) after recrystallization from a mixture of dimethylformamide and water (2:1).

Analysis (%) for $C_9H_9N_3O_2S$:

| calculated: | C 48.42; | H 4.06; | N 18.82; | S 14.36. |
|---|---|---|---|---|
| found: | C 48.16; | H 3.94; | N 18.50; | S 14.61. |

EXAMPLE 6

12.7 g of anhydrous sodium carbonate dissolved in 200 ml of water were added to a suspension of 44.6 g of 1-amino-5-methoxycarbonylbenzimidazole-2-thione in 400 ml of dioxane, then a solution containing 68 g of 4-chloro-3-(N-dimethylaminomethylidene)sulfamoylbenzoyl chloride in 400 ml of dioxane was added dropwise to the above mixture while stirring and cooling by cold water to a temperature between 15° C. and 20° C. After completing the addition, the reaction mixture was stirred at 20° C. for 2 hours, then filtered to give a clear solution. The filtrate was diluted with 2 liters of water, the crystalline precipitate was filtered by suction, washed with water and dried at 80° C. The crude product obtained (84.5 g) was dissolved by boiling in 355 ml of glacial acetic acid and then diluted as hot with 1 liter of water under vigorous stirring. After cooling down, the crystalline precipitate was filtered by suction, washed with water and dried at 80° C. to yield 74.4 g (75.5%) of 1-[4'-chloro-3'-(N-dimethylaminomethylidene)sulfamoylbenzoyl]amino-4-methoxycarbonylbenzimidazole-2-thione, as a white powder, m.p.: 238°–239° C. (with decomposition).

Analysis (%) for $C_{19}H_{18}ClN_5O_5S_2$:

| calculated: | C 45.91; | H 3.85; | N 14.10; | Cl 7.13; | S 12.90. |
|---|---|---|---|---|---|
| found: | C 45.45; | H 3.59; | N 13.95; | Cl 7.10; | S 13.16. |

86.8 g of the compound prepared above were stirred with 500 ml of 2N sodium hydroxide solution at 50° C. for 8 hours, then the solution was clarified by activated carbon, filtered and the pH value of the filtrate was adjusted to 6 by adding 2N hydrochloric acid while cooling and stirring vigorously. After adding 100 ml of ethanol, the precipitate was filtered by suction, washed with water and dried at 80° C. to give 60.8 g (81.4%) of 1-(4'-chloro-3'-sulfamoylbenzoyl)amino-5-carboxybenzimidazole-2-thione, m.p.: 285°–290° C. (with decomposition). After purifying as described in Example 1, both substances proved to be completely identical.

EXAMPLE 7

After adding 3.66 g of N,N'-di(methoxycarbonyl)-S-methylisothiourea to a solution of 2.06 g of 2-amino-4-methoxycarbonyl-N-(4'-chloro-3'-sulfamoylbenzoyl)-phenylhydrazine in 10 ml of dimethylformamide, the solution obtained was boiled for 3 hours, then evaporated under reduced pressure. The residue was dissolved in 10 ml of warm glacial acetic acid, clarified by activated carbon, filtered and the filtrate was poured into 100 ml of water. The separated crystals are filtered by suction, washed with water and dried at 80° C. to yield 3.7 g (87%) of 1-(4'-chloro-3'-sulfamoylbenzoyl)amino-5-methoxycarbonylbenzimidazolone, m.p.: 210°–216° C. (with decomposition).

3.7 g of the benzimidazolone derivative obtained above were stirred with 37 ml of 2N sodium hydroxide solution at 60° C. for 5 hours, then clarified by activated carbon, filtered and the filtrate was acidified by 2N hydrochloric acid. The crystalline precipitate was filtered by suction, washed with water and dried at 80° C. Thus, 2.6 g (72%) of 1-(4'-chloro-3'-sulfamoylbenzoyl)-amino-5-carboxybenzimidazolone were obtained as a beige crystalline solid, m.p.: 339° C. after recrystallization from 50% aqueous ethanol.

Analysis (%) for $C_{15}H_{11}ClN_4O_6S$:

| calculated: | C 43.85; | H 2.70; | N 13.64; | S 7.80; |
|---|---|---|---|---|
| found: | C 43.57; | H 2.86; | N 13.58; | S 7.42. |

EXAMPLE 8

11 g 1-(4'-chloro-3'-sulfamoylbenzoyl)-amino-5-methoxycarbonylbenzimidazole-2-thione were dissolved in a solution prepared from 0.58 g of sodium metal and 100 ml of methanol. After adding 1.56 ml of methyl iodide, the solution was refluxed for 3 hours, then methano was evaporated and the residue was triturated with water. The powder-like crystals were filtered by suction, washed with water and dried at 80° C. to yield 10.8 g (95%) of 1-(4'-chloro-3'-sulfamoylbenzoyl)amino-5-methoxycarbonyl-2-methylthiobenzimidazole, m.p.: 186°–188° C. (with decomposition).

Analysis (%) for $C_{17}H_{15}ClN_4O_5S_2$:

| calculated: | C 44.88; | H 3.32; | N 12.32; | Cl 7.79; | S 14.10; |
|---|---|---|---|---|---|
| found: | C 44.75; | H 3.68; | N 12.50; | Cl 7.60; | S 13.91. |

EXAMPLE 9

10 g of the ester compound prepared according to Example 8 were hydrolyzed by using 50 ml of 2N sodium hydroxide solution as described in Example 1. Thus, 9 g (94%) of 1-(4'-chloro-3'-sulfamoylbenzoyl)-amino-5-carboxy-2-methylthiobenzimidazole were obtained which was recrystallized from 50% aqueous ethanol to give the substance with 1.5 molecule of crystal water, m.p.: 214°–222° C. (with decomposition).

Analysis (%) for $C_{16}H_{13}ClN_4O_5S_2 \cdot 1.5H_2O$:

| calculated: | C 41.06; | H 3.44; | N 11.97; | Cl 7.57; | S 13.07; |
|---|---|---|---|---|---|
| found: | C 41.00; | H 3.35; | N 11.71; | Cl 7.11; | S 13.15. |

EXAMPLE 10

6.6 g of 1-(4'-chloro-3'-sulfamoylbenzoyl)-amino-5-methoxycarbonylbenzimidazole-2-thione were dissolved in a solution prepared from 0.35 g sodium metal and 60 ml of methanol. After adding 2 ml of benzyl chloride the reaction mixture was refluxed under stirring for 16 hours, then evaporated under reduced pressure. The residue was triturated with water, the solid product was filtered and subjected to column chromatography after drying. Silicagel was used as sorbent and a mixture of benzene and acetone (2:1) served as eluent. Thus, 5.37 g (67.8%) of 2-benzylthio-1-(4'-chloro-3'-sulfamoylbenzoyl)amino-5-methoxycarbonylbenzimidazole were obtained in the form of a white powdery solid, m.p.: 111°–118° C. (with decomposition). The $R_f$ value of this product was 0.90 by thin layer chromatography (TLC) using a developing system of chloroform/acetic acid/methanol.

Analysis (%) for $C_{23}H_{19}ClN_4O_5S_2$:

| calculated: | C 52.02; | H 3.61; | N 10.55; | Cl 6.68; | S 12.08; |
|---|---|---|---|---|---|
| found: | C 52.32; | H 4.00; | N 9.90; | Cl 6.00; | S 12.00. |

EXAMPLE 11

A suspension containing 5.3 g of 2-benzylthio-1-(4'-chloro-3'-sulfamoylbenzoyl)amino-5-methoxycarbonylbenzimidazole in 30 ml of 2N sodium hydroxide solution was stirred at 50° C. for 4 hours. Meanwhile most part of the starting substance dissolved. After filtering off the insoluble part, the filtrate was neutralized by adding 30 ml of 2N hydrochloric acid. The white precipitate was filtered by suction, washed with water and dried to yield 4.9 g (94.8%) of 2-benzylthio-1-(4'-chloro-3'-sulfamoylbenzoyl)amino-5-carboxybenzimidazole, m.p.: 190°–196° C. (with decomposition).

Analysis (%) for $C_{23}H_{19}ClN_4O_5S_2$:

| calculated: | C 51.10; | H 3.31; | N 10.84; | Cl 6.86; | S 12.40; |
|---|---|---|---|---|---|
| found: | C 49.23; | H 3.77; | N 11.00; | Cl 6.84; | S 11.40. |

EXAMPLE 12

3.85 ml of 35% hydrogen peroxide solution were dropped at 20° C. to a suspension of 9 g of 1-(4'-chloro-3'-sulfamoylbenzoyl)amino-2-methylthio-5-methoxycarbonylbenzimidazole in 20 ml of glacial acetic acid, then the reaction mixture was stirred in a hot water bath for 90 minutes. After cooling down, the solid product was filtered by suction, washed with water and dried to give 6.4 g (65.7%) of 1-(4'-chloro-3'-sulfamoylbenzoyl)amino-5-methoxycarbonyl-2-methylsulfonylbenzimidazole in the form of a white powder, m.p.: 254°–255° C. (with decomposition) after recrystallization from a mixture of dimethylformamide and water (1:1).

Analysis (%) for $C_{17}H_{15}ClN_4O_4S_2$:

| calculated: | C 41.93; | H 3.10; | N 11.50; | Cl 7.28; | S 13.17; |
|---|---|---|---|---|---|
| found: | C 42.01; | H 3.15; | N 11.34; | Cl 7.35; | S 13.01. |

EXAMPLE 13

A suspension containing 5.4 g of 1-(4'-chloro-3'-sulfamoylbenzoyl)amino-5-methoxycarbonyl-2-methylsulfonylbenzimidazole in 30 ml of 2N sodium hydroxide solution was stirred at 50° C. for 4 hours to give a clear violet solution which was clarified by activated carbon, filtered and the filtrate was acidified to pH 2 by adding 2N hydrochloric acid. The white precipitate was filtered by suction, washed with water and dried to give 4.43 g (85.7%) of 5-carboxy-1-(4'-chloro-3'-sulfamoylbenzoyl)amino-2-methylsulfonylbenzimidazole, as a white powdery solid, m.p.: 222°–225° C. (with decomposition) which is not changed after recrystallization from a mixture of dimethylformamide and water (3:2).

Analysis (%) for $C_{16}H_{23}ClN_4O_7S_2$:

| calculated: | C 40.64; | H 2.77; | N 11.85; | Cl 7.50; | S 13.56; |
|---|---|---|---|---|---|
| found: | C 40.07; | H 3.01; | N 12.02; | Cl 7.65; | S 13.29. |

EXAMPLE 14

17.25 g of 4-chloro-3-(N-dimethylaminomethylidene)sulfamoylbenzoyl chloride were added to a suspension of 11.45 g of 1-amino-5-methoxycarbonyl-2-methylbenzimidazole in 25 ml of pyridine, then the reaction mixture was heated to about 60° to 70° C. to give a yellow solution. The thick yellow mixture was set aside overnight, then 200 ml of water were added. The separated yellow gum disaggregated to a beige powder after stirring for some minutes. The product was filtered by suction, washed with water and dried to give 23.9 g (90%) of 1-[4'-chloro-3'-(N-dimethylaminomethylidene)sulfamoylbenzoyl]amino-5-methoxycarbonyl-2-methylbenzimidazole, m.p.: 240°–245° C. (with decomposition). After recrystallization from nitromethane, the substance melted at 260° to 263° C. (with decomposition).

Analysis (%) for $C_{20}H_{20}ClN_5O_5S$:

| calculated: | C 50.26; | H 4.22; | N 14.65; | Cl 7.42; | S 6.71; |
|---|---|---|---|---|---|
| found: | C 49.85; | H 4.31; | N 15.12; | Cl 7.44; | S 6.52. |

Preparation of starting materials (A) 235 ml of acetic anhydride were added to a suspension of 97.5 g of 2-amino-4-carboxy-N-acetylphenylhydrazine in 450 ml of dichloromethane while stirring. The mixture was stirred at room temperature for 3 hours, then the crystals were filtered by suction, washed with dichloromethane and dried at 60° C. Thus, 101.2 g (86.5%) of 2-acetylamino-4-carboxy-N-acetylphenylhydrazine were obtained, m.p.: 238° C. (with decomposition).

Analysis (%) for $C_{11}H_{13}N_3O_4$:

| calculated: | C 52.58; | H 5.21; | N 16.93; |
|---|---|---|---|
| found: | C 52.82; | H 5.12; | N 17.20. |

(B) 101.2 g of the acetyl derivative prepared according to Example 14(A) were boiled with 800 ml of acetoc acid for 13 hours, then evaporated under reduced pressure. After mixing the residue with 800 ml of water, the crystalline precipitate was filtered by suction, washed with water and dried at 80° C. to yield 73.1 g (78.5%) of 1-acetylamino-5-carboxy-2-methylbenzimidazole, as a white powdery solid, m.p.: 293°–294° C. (with decomposition).

Analysis (%) for $C_{11}H_{11}N_3O_3$:

| calculated: | C 56.65; | H 4.75; | N 18.02; |
|---|---|---|---|
| found: | C 56.71; | H 4.62; | N 17.89. |

(C) 73.1 g of the benzimidazole derivative prepared according to the Example 14(B) were boiled with 310 ml of 2N hydrochloric acid for 5 hours. The hot solution thus obtained was clarified by activated carbon and filtered. After cooling down, the crystalline precipitate was filtered by suction, washed with a little volume of water and dried at 80° C. to yield 68.9 g (96%) of 1- amino-5-carboxy-2-methylbenzimidazole hydrochloride in the form of snow-white glistening platelets, m.p.: 287°–288° C. (with decomposition).

Analysis (%) for C$_9$H$_{10}$ClN$_3$O$_2$:

| calculated: | C 47.48; | H 4.43; | N 18.46; | Cl 15.17; |
|---|---|---|---|---|
| found: | C 47.85; | H 4.83; | N 18.15; | Cl 15.20. |

(D) 68.1 g of the hydrochloride prepared according to Example 14(C) were suspended in 1 liter of methanol. Further on, the process described in Example 5(F) was repeated to obtain 48 g (78%) of 1-amino-5-methoxycarbonyl-2-methylbenzimidazole, m.p.: 220°–222° C.

Analysis (%) for C$_{10}$H$_{11}$N$_3$O$_2$:

| calculated: | C 58.53; | H 5.40; | N 20.48; |
|---|---|---|---|
| found: | C 58.10; | H 5.38; | N 20.25. |

(E) To a suspension containing 14.5 g of 4-chloro-3-(N-dimethylaminomethylidene)sulfamoylbenzoic acid (prepared according to NL-PS No. 7,604,356) in 50 ml of thionyl chloride, 2 drops of dimethylformamide were added, the reaction mixture was refluxed while stirring for 2 hours, then filtered to obtain a clear solution. The filtrate was evaporated under reduced pressure to yield 12.7 g (82%) of 4-chloro-3-(N-dimethylaminomethylidene)-sulfamoylbenzoyl chloride, as a snow-white solid, m.p.: 140° C. After recrystallization from benzene, the m.p. was raised to 154°–155° C.

Analysis (%) for C$_{10}$H$_{10}$Cl$_2$N$_2$O$_3$S:

| calculated: | C 38.84; | H 3.26; | N 9.06; | Cl 22.93; | S 10.37; |
|---|---|---|---|---|---|
| found: | C 38.28; | H 3.07; | N 8.94; | Cl 23.14; | S 10.58. |

EXAMPLE 15

A mixture containing 25 g of 2-amino-4-methoxycarbonyl-N-[4'-chloro-3'-(N-dimethylaminomethylidene)-sulfamoylbenzoyl]phenylhydrazine in 80 ml of acetic anhydride was kept at room temperature overnight, then mixed with 250 ml of water. The crystals were filtered by suction, washed with water and dried to give 26 g of 2-acetylamino-4-methoxycarbonyl-N-[4'-chloro-3'-(N-dimethylaminomethylidene)sulfamoylbenzoyl]-phenylhydrazine, m.p.: 218°–220° C. (with decomposition).

26 g of the product thus obtained were boiled with 200 ml of glacial acetic acid for 5 hours. The clear yellow solution was evaporated under reduced pressure and the residue was triturated with water. The separated crystals were filtered by suction, washed with water and dried. Thus, 24.5 g (98% calculated for the starting amino compound) of 1-[4'-chloro-3'-(N-dimethylaminomethylidene)sulfamoylbenzoyl]amino-5-methoxycarbonyl-2-methylbenzimidazole were obtained in the form of a beige powder, m.p.: 245°–255° C. (with decomposition). The m.p. was raised to 260°–263° C. after recrystallization from nitromethane. This product was in all respects identical with that obtained according to Example 14.

Preparation of starting materials (A) 17.75 g of crystalline sodium carbonate dissolved in 330 ml of water were added to a suspension of 70.76 g of 4-methoxycarbonyl-2-nitrophenylhydrazine in 670 ml of dioxane. 103.6 g of 4-chloro-3-(N-dimethylaminomethylidene)sulfamoylbenzoyl chloride dissolved in 280 ml of dioxane were dropped to the above mixture under stirring to give a dark clear solution. The pH value of the reaction mixture was controlled from time to time and maintained at about 7 by portionwise adding 1N sodium bicarbonate solution. After completing the addition, the mixture was stirred for an additional 1 hour, then diluted with 1 liter of water. The precipitate was filtered by suction, washed with water and dried at 80° C. to give 127.8 g (78.8%) of 4-methoxycarbonyl-2-nitro-N-[4'-chloro-3'-(N-dimethylaminomethylidene)sulfamoylbenzoyl]phenylhydrazine, m.p.: 243°–247° C. The m.p. was raised to 255°–256° C. after recrystallization from nitromethane.

Analysis (%) for C$_{18}$H$_{18}$ClN$_5$O$_7$S:

| calculated: | C 44.68; | H 3.75; | N 14.47; | Cl 7.33; | S 6.63; |
|---|---|---|---|---|---|
| found: | C 44.70; | H 3.69; | N 14.70; | Cl 7.53; | S 6.79. |

(B) 5 g of 10% palladium-on-carbon catalyst were added to a suspension of 61 g of the nitro compound prepared according to Example 15(A) in 40 ml of 96% ethanol. The mixture was heated to 60° to 70° C. and 250 ml of 30% aqueous sodium hypophosphite solution were added dropwise at the same temperature at such a rate that the violent foaming was avoided. After completing the addition, the mixture was stirred for additional 30 minutes at 60° to 70° C. After cooling down, the mixture was filtered, the solid product was mixed with 250 ml of dioxane, filtered and the filtrate was evaporated under reduced pressure. After triturating the residue with 200 ml of 50% aqueous ethanol, the crystals were filtered by suction, washed with 50% ethanol and dried at 80° C. Thus, 40 g (68%) of 2-amino-4-methoxycarbonyl-N-[4'-chloro-3'-(N-dimethylaminomethylidene)sulfamoylbenzoyl]-phenylhydrazine were obtained in the form of butter-colored crystals, m.p.: 219°–220° C. (with decomposition).

Analysis (%) for C$_{18}$H$_{20}$ClN$_5$O$_5$S:

| calculated: | C 47.63; | H 4.44; | N 15.43; | Cl 7.81; |
|---|---|---|---|---|
| found: | C 47.80; | H 4.25; | N 15.44; | Cl 7.41. |

EXAMPLE 16

23.9 g 1-[4'-chloro-3'-(N-dimethylaminomethylidene)sulfamoylbenzoyl]amino-5-methoxycarbonyl-2-methylbenzimidazole were stirred with 150 ml of 2N sodium hydroxide solution at 50° C. until the ammonia formation ceased. During this period a yellow solution was obtained. After cooling down, the solution was acidified to pH 1 by 2N hydrochloric acid. The precipitate was filtered by suction, washed with water and dried to yield 19.8 g (97%) of white powder-like 1-(4'-chloro-3'-sulfamoylbenzoyl)amino-5-carboxy-2-methylbenzimidazole, m.p.: 293°–296° C. (with decomposition) after recrystallization from 50% aqueous ethanol.

Analysis (%) for C$_{16}$H$_{13}$ClN$_4$O$_5$S:

| calculated: | C 47.00; | H 3.20; | N 13.71; | Cl 8.67; | S 7.85; |
|---|---|---|---|---|---|
| found: | C 45.80; | H 3.71; | N 13.93; | Cl 8.80; | S 7.74. |

EXAMPLE 17

The process of Example 14 was repeated, except that 10.63 g of 1-amino-5-methoxycarbonylbenzimidazole were used as starting compound to obtain 21.1 g (82%) of 1-[4'-chloro-3'-(N-dimethylaminomethylidene)-sulfamoylbenzoyl]amino-5-methoxycarbonylbenzimidazole in the form of a pale yellow powder, m.p.: 249°–252° C. (with decomposition).

Analysis (%) for $C_{19}H_{18}ClN_5S$:

| | | | | |
|---|---|---|---|---|
| calculated: | C 49.19; | H 3.91; | N 15.10; | S 6.91; |
| found: | C 49.62; | H 4.36; | N 15.30; | S 6.68. |

Preparation of the starting materials (A) 2.5 g of 10% palladium-on-carbon catalyst were added to a solution of 25.3 g of 4-methoxycarbonyl-2-nitro-N-acetylphenylhydrazine in 380 ml of methoxyethanol and the mixture was hydrogenated in a shaking equipment until the hydrogen uptake ceased. After filtering off the catalyst, the filtrate was evaporated under reduced pressure and the residue was mixed with 100 ml of water. The separated crystals were filtered by suction, washed with water and dried at 80° C. Thus, 19.1 g (85.6%) of 2-amino-4-methoxycarbonyl-N-acetylphenylhydrazine were obtained as a beige crystalline solid, m.p.: 175°–178° C. After recrystallization from methanol, the m.p. was raised to 180°–182° C.

Analysis (%) for $C_{10}H_{13}N_3O_3$:

| | | | |
|---|---|---|---|
| calculated: | C 53.80; | H 5.87; | N 18.82; |
| found: | C 53.17; | H 5.94; | N 18.93. |

(B) After refluxing 22.3 g of phenylhydrazine derivative prepared according to Example 17(A) with 150 ml of anhydrous formic acid for 5 hours, the transparent violet-coloured solution was evaporated under reduced pressure. By pouring 250 ml of water to the residual gum, a solution was obtained and white crystals soon started to separate. After standing for several hours, the crystals were filtered by suction, washed with water and dried at 80° C. to yield 17.2 g (76%) of 1-acetylamino-5-methoxycarbonylbenzimidazole in the form of white crystalline solid, m.p.: 210°–212° C. (with decomposition).

Analysis (%) for $C_{11}H_{11}N_3O_3$:

| | | | |
|---|---|---|---|
| calculated: | C 56.65; | H 4.75; | N 18.02; |
| found: | C 56.55; | H 4.67; | N 18.28. |

(C) 32.5 g of the benzimidazole derivative prepared according to Example 17(B) were boiled with 140 ml of 2N hydrochloric acid for 5 hours. After clarifying the solution by activated carbon and filtering and cooling down, the white crystalline precipitate was filtered by suction, washed with a little water and dried at 80° C. Thus, 23.2 g (78%) of 1-amino-5-carboxybenzimidazole hydrochloride were obtained, as a snow-white crystalline solid, m.p.: 325°–330° C.

Analysis (%) for $C_8H_8ClN_3O_2$:

| | | | | |
|---|---|---|---|---|
| calculated: | C 44.98; | H 3.77; | N 19.67; | Cl 16.60; |
| found: | C 44.49; | H 3.80; | N 19.68; | Cl 16.52. |

(D) 26 g of the benzimidazole derivative prepared according to Example 17(C) were reacted with 270 ml of methanol containing hydrogen chloride as described in Example 5(F). For decomposing the hydrochloride thus obtained, 220 ml of 1N sodium bicarbonate solution were used. Thus, 19.3 g (83%) of 1-amino-5-methoxycarbonylbenzimidazole were obtained, m.p.: 194°–195° C.

Analysis (%) for $C_9H_9N_3O_2$:

| | | | |
|---|---|---|---|
| calculated: | C 56.54; | H 4.75; | N 21.98; |
| found: | C 56.95; | H 4.63; | N 21.62. |

EXAMPLE 18

28.7 g of 2-amino-4-methoxycarbonyl-N-[4'-chloro-3'-(N-dimethylaminomethylidene)sulfamoylbenzoyl]-phenylhydrazine were boiled with 200 ml of anhydrous formic acid for 6 hours. After evaporating the solution under reduced pressure, the residue was triturated with water, the separated crystals were filtered by suction, washed with water and dried to yield 19 g (64%) of 1-[4'-chloro-3'-(N-dimethylaminomethylidene)sulfamoylbenzoyl]amino-5-methoxycarbonylbenzimidazole in the form of a yellowish-beige powder, m.p.: 240°–253° C. (with decomposition). This product was in all respects identical with that of Example 17.

EXAMPLE 19

The process of Example 16 was followed, except that 6.4 g of 1-[4'-chloro-3'-(N-dimethylaminomethylidene)-sulfamoylbenzoyl]amino-5-methoxycarbonylbenzimidazole and 40 ml of 2N sodium hydroxide solution were used as starting materials. Thus, 5.1 g (92%) of 1-(4'-chloro-3'-sulfamoylbenzoyl)amino-5-carboxybenzimidazole were obtained, m.p.: 290°–291° C. (with decomposition) after recrystallization from 50% aqueous ethanol.

Analysis (%) for $C_{15}H_{11}ClN_4O_5S$:

| | | | | | |
|---|---|---|---|---|---|
| calculated: | C 45.63; | H 2.81; | N 14.19; | Cl 8.98; | 8.12; |
| found: | C 45.27; | H 2.79; | N 13.85; | Cl 8.93; | S 7.71. |

EXAMPLE 20

The process of Example 1 was followed but 2.32 g of 2-amino-4-cyano-N-(4'-chloro-3'-sulfamoylbenzoyl)-phenylhydrazine, 10 ml of methanol, 2.52 ml of carbon disulfide, 1.07 g of potassium hydroxide and 4.5 ml of abs. ethanol were used as starting materials. The reaction mixture was acidified by adding 24 ml of acetic acid. Thus, 2.32 g (97%) of crude product were obtained which was purified by chromatography on a silicagel column using a mixture of benzene and acetone (1:1) as eluent. Thus, 1-(4'-chloro-3'-sulfamoylbenzoyl)amino-5-cyanobenzimidazole-2-thione was obtained, m.p.: 315° C.

Analysis (%) for $C_{15}H_{10}ClN_5O_3S_2$:

| | | | | | |
|---|---|---|---|---|---|
| calculated: | C 44.16; | H 2.47; | N 17.17; | Cl 8.69; | S 15.72; |

-continued

| | | | | | |
|---|---|---|---|---|---|
| found: | C 44.40; | H 2.67; | N 16.94; | Cl 8.96; | S 15.33. |

Preparation of the starting materials (A) The process described in Example 1(B) was followed and 8.1 g of 4-cyano-2-nitrophenylhydrazine (prepared as described in: Beilst. 9 Vol. II page 289), 114 ml of dioxane, 46 ml aqueous solution of 2.4 g of crystalline sodium carbonate and 11.6 g of 4-chloro-3-sulfamoylbenzoyl chloride dissolved in 53 ml of dioxane were used as starting materials. After evaporating the reaction mixture, the residue was thoroughly mixed with water, the yellow precipitate was filtered by suction, washed with water and dried at 80° C. Thus, 3.75 g (65%) of 4-cyano-2-nitro-N-(4'-chloro-3'-sulfamoylbenzoyl)-phenylhydrazine were obtained, m.p.: 292°–295° C. (with decomposition) after recrystallization from acetic acid.

Analysis (%) for $C_{14}H_{10}ClN_5O_5S \cdot \frac{1}{2} CH_3COOH$:

| | | | | | |
|---|---|---|---|---|---|
| calculated: | C 40.63; | H 2.92; | N 16.92; | Cl 8.57; | S 7.78; |
| found: | C 40.06; | H 2.52; | N 16.85; | Cl 8.23; | S 7.65. |

(B) 1 g of Raney nickel catalyst was added to 8.54 g of the nitro compound [prepared according to Example 20(A)] dissolved in 500 ml of methoxyethanol, then the mixture was hydrogenated under atmospheric pressure at room temperature in a shaking equipment until the hydrogen uptake ceased. After filtering off the catalyst and evaporating the filtrate under reduced pressure, the residue was triturated with water, the white crystalline precipitate was filtered by suction, washed with water and dried at 80° C. Thus, 6.52 g (80%) of 2-amino-4-cyano-N-(4'-chloro-3'-sulfamoylbenzoyl)phenylhydrazine were obtained, m.p.: 205° C. (with decomposition).

Analysis (%) for $C_{14}H_{12}ClN_5O_3S$:

| | | | | | |
|---|---|---|---|---|---|
| calculated: | C 45.96; | H 3.31; | N 19.15; | Cl 9.69; | S 8.77. |
| found: | C 46.06; | H 3.28; | N 19.21; | Cl 9.81; | S 8.80. |

EXAMPLE 21

The process of Example 1 was followed by using 2.9 g of 2-amino-4-benzoyl-N-(4'-chloro-3'-sulfamoylbenzoyl)phenylhydrazine, 10 ml of methanol, 2.8 ml of carbon disulfide und 1.2 g of potassium hydroxide dissolved in 4.5 ml of abs. ethanol as starting materials. For acidifying the reaction mixture, 24 ml of acetic acid were used. After recrystallization of the crude product as a wet filter cake from 96% ethanol, 1.7 g (57%) of 5-benzoyl-1-(4'-chloro-3'-sulfamoylbenzoyl)aminobenzimidazole-2-thione were obtained, m.p.: 233° C. (with decomposition).

Analysis (%) for $C_{21}H_{15}ClN_4O_4S_2$:

| | | | | | |
|---|---|---|---|---|---|
| calculated: | C 51.79; | H 3.11; | N 11.51; | Cl 7.28; | S 13.17; |
| found: | C 51.30; | H 3.74; | N 11.39; | Cl 7.40; | S 13.50. |

Preparation of the starting materials (A) 20 ml of hydrazine hydrate were added to the suspension of 52.33 g of 4-chloro-3-nitrobenzophenone in 200 ml of abs. ethanol under stirring. The reaction mixture was stirred at room temperature for 75 minutes, then slowly heated to the boiling point. After completion of the violent reaction, the mixture was refluxed for an additional 1 hour. After cooling down, the crystals were filtered by suction, thoroughly washed with water and dried at 80° C. Thus, 38.62 g (75%) of 4-benzoyl-2-nitrophenylhydrazine were obtained as orange-red crystals, m.p.: 163°–164° C.

Analysis (%) for $C_{13}H_{11}N_3O_3$:

| | | | |
|---|---|---|---|
| calculated: | C 60.69; | H 4.31; | N 16.33; |
| found: | C 60.60; | H 4.15; | N 16.40. |

(B) By using the process of Example 1(B), 28 g of 4-benzoyl-2-nitrophenylhydrazine, 272 ml of dioxane, 5.8 g of anhydrous sodium carbonate dissolved in 110 ml of water and 27.6 g of 4-chloro-3-sulfamoylbenzoyl chloride dissolved in 217 ml of dioxane were used as starting materials to yield 29.1 g (61%) of 4-benzoyl-2-nitro-N-(4'-chloro-3'-sulfamoylbenzoyl)phenylhydrazine, m.p.: 148° C. after recrystallization from methanol.

Analysis (%) for $C_{20}H_{15}ClN_4O_6S$:

| | | | | | |
|---|---|---|---|---|---|
| calculated: | C 50.58; | H 3.18; | N 11.80; | Cl 7.47; | S 6.75; |
| found: | C 49.59; | H 3.15; | N 11.46; | Cl 7.71; | S 6.46. |

(C) By using the process of Example 20(B), and 23.7 g of the nitro compound [prepared as described in Example 21(B)] and 500 ml of methanol as starting materials, 19.7 g (88.5%) of 2-amino-4-benzoyl-N-(4'-chloro-3'-sulfamoylbenzoyl)phenylhydrazine were obtained, m.p.: 162° C. (with decomposition).

Analysis (%) for $C_{20}H_{17}ClN_4O_4S$:

| | | | | | |
|---|---|---|---|---|---|
| calculated: | C 53.99; | H 3.85; | N 12.59; | Cl 7.97; | S 7.21; |
| found: | C 53.80; | H 3.94; | N 12.87; | Cl 7.71; | S 7.43. |

EXAMPLE 22

The process of Example 16 was followed by using 6.2 g of 1-[4'-chloro-3'-(N-dimethylaminomethylidene)sulfamoylbenzoyl]amino-benzimidazole and 40 ml of 2N sodium hydroxide solution as starting materials to yield 6 g (87.6%) of 1-(4'-chloro-3'-sulfamoylbenzoyl)-aminobenzimidazole, m.p.: 162° C. (with decomposition) after recrystallization from 96% ethanol.

Analysis (%) for $C_{14}H_{11}ClN_4O_3S$:

| | | | | | |
|---|---|---|---|---|---|
| calculated: | C 47.93; | H 3.16; | N 15.97; | Cl 10.11; | S 9.14; |
| found: | C 47.50; | H 3.08; | N 15.70; | Cl 9.95; | S 8.96. |

Preparation of the starting material

The process of Example 14 was followed by using 4 g of 1-aminobenzimidazole [prepared as described in: J. Org. Chem. 28, 736 (1963)], 7 ml of pyridine and 9.3 g of 4-chloro-3-(N-dimethylaminomethylidene)sulfamoylbenzoyl chloride as starting materials to yield 11.1 g (91%) of 1-[4'-chloro-3'-(N-dimethylaminomethylidene)sulfamoylbenzoyl]aminobenzimidazole, m.p.: 258°–261° C. after recrystallization from nitromethane.

Analysis (%) for $C_{17}H_{16}ClN_5O_3S$:

| | | | | | |
|---|---|---|---|---|---|
| calculated: | C 50.30; | H 3.97; | N 17.26; | Cl 8.74; | S 7.90; |

| | | | | | |
|---|---|---|---|---|---|
| found: | C 50.13; | H 4.01; | N 17.27; | Cl 8.90; | S 8.03. |

| | | | | |
|---|---|---|---|---|
| calculated: | C 31.03; | H 3.47; | N 24.13; | S 13.81; |
| found: | C 31.50; | H 3.48; | N 24.37; | S 13.57. |

EXAMPLE 23

The process of Example 16 was followed by using 5.1 g of 1-[4'-chloro-3'-(N-dimethylaminomethylidene)sulfamoylbenzoyl]amino-2-methylbenzimidazole and 30 ml of 2N sodium hydroxide solution as starting materials to yield 3:7 g (87%) of 1-(4'-chloro-3'-sulfamoylbenzoyl)amino-2-methylbenzimidazole, m.p.: 300° C. (with decomposition) after recrystallization from a mixture of dimethylformamide and water (1:1).

Analysis (%) $C_{15}H_{13}ClN_4O_3S$:

| | | | | | |
|---|---|---|---|---|---|
| calculated: | C 49.38; | H 3.59; | N 15.36; | Cl 9.72; | S 8.79; |
| found: | C 49.18; | H 3.56; | N 15.20; | Cl 9.72; | S 8.98. |

Preparation of the starting material

The process of Example 14 was followed by using 4.1 g of 1-amino-2-methylbenzimidazole [prepared as described in: J. Org. Chem. 28, 736 (1963)] 15 ml of pyridine and 9.3 g of 4-chloro-3-(N-dimethylaminomethylidene)sulfamoylbenzoyl chloride to obtain 10.2 g (77.6%) of 1-[4'-chloro-3'-(N-dimethylaminomethylidene)sulfamoylbenzoyl]amino-2-methylbenzimidazole hydrate, m.p.: 166° C. (with decomposition) after recrystallization from 96% of aqueous ethanol. After recrystallization from acetonitrile, the product melted at 232°–235° C.

Analysis (%) for $C_{18}H_{18}ClN_5O_3S$:

| | | | | | |
|---|---|---|---|---|---|
| calculated: | C 49.36; | H 4.60; | N 15.99; | Cl 8.10; | S 7.01; |
| found: | C 49.25; | H 4.61; | N 15.72; | Cl 8.10; | S 7.10. |

EXAMPLE 24

The process of Example 16 was followed by using 2.4 g of 1-[4'-chloro-3'-(N-dimethylaminomethylidene)sulfamoylbenzoyl]amino-5-sulfamoylbenzimidazole-2-thione and 12 ml of 2N sodium hydroxide solution as starting materials to yield 1.64 g (76%) of 1-(4'-chloro-3'-sulfamoylbenzoyl)amino-5-sulfamoylbenzimidazole-2-thione, m.p.: 326° C. (with decomposition) after thoroughly boiling out with ethanol.

Analysis (%) for $C_{14}H_{12}ClN_5O_5S_2$:

| | | | | | |
|---|---|---|---|---|---|
| calculated: | C 36.40; | H 2.62; | N 15.16; | Cl 7.68; | S 20.82; |
| found: | C 36.31; | H 2.45; | N 15.66; | Cl 7.36; | S 20.80. |

Preparation of the starting materials (A) 20 ml of hydrazine hydrate were added to a suspension of 47.33 g of 4-chloro-3-nitrobenzenesulfonamide [prepared as described in: J. Am. Chem. Soc. 73, 2558 (1951)] in 200 ml of abs. ethanol. The mixture was boiled under stirring for 30 minutes, then cooled down. The crystals were filtered by suction and thoroughly washed with water to obtain 43.38 g (93.4%) of 2-nitro-4-sulfamoylphenylhydrazine, m.p.: 217°–218° C. (with decomposition).

Analysis (%) for $C_6H_8N_4O_4S$:

(B) The process of Example 1(B) was followed by using 65.7 g of the nitro compound prepared according to Example 24(A), 700 ml of dioxane, 15 g of anhydrous sodium carbonate dissolved in 280 ml of water and 87.5 g of 4-chloro-3-(N-dimethylaminomethylidene)sulfamoylbenzoyl chloride dissolved in 560 ml of dioxane. After evaporating the reaction mixture under reduced pressure, the residue was thoroughly mixed with water, the solid product was filtered by suction and the wet filter cake was boiled out with 600 ml of methanol. After filtering and drying, 121.5 g (85%) of 2-nitro-4-sulfamoyl-N-[4'-chloro-3'-(N-dimethylaminomethylidene)-sulfamoylbenzoyl]phenylhydrazine were obtained, m.p.: 248° C. (with decomposition). After recrystallization from glacial acetic acid, the product melted at 252° C. (with decomposition).

Analysis (%) for $C_{16}H_{17}ClN_6O_7S_2$:

| | | | | | |
|---|---|---|---|---|---|
| calculated: | C 38.06; | H 3.39; | N 16.64; | Cl 7.02; | S 12.70; |
| found: | C 38.10; | H 3.42; | N 16.59; | Cl 7.00; | S 12.68. |

(C) The process of Example 15(B) was followed by using 5 g of the nitro compound prepared according to Example 24(B), 60 ml of abs. ethanol, 0.5 g of 10% palladium-on-carbon catalyst and 30 ml of 30% aqueous sodium hypophosphite solution as starting materials. Thus, 4.2 g (88%) of 2-amino-4-sulfamoyl-N-[4'-chloro-3'-(N-dimethylaminomethylidene)sulfamoylbenzoyl]-phenylhydrazine were obtained, m.p.: 152° C. (with decomposition).

(D) The process of Example 3 was followed by using 4.75 g of the phenylhydrazine derivative prepared according to Example 24(C), 20 ml of pyridine and 1.6 g of potassium ethyl xanthate as starting materials. Thus, 3.2 g (62%) of 1-[4'-chloro-3'-(N-dimethylaminomethylidene)sulfamoylbenzoyl]amino-5-sulfamoylbenzimidazole-2-thione were obtained, m.p.: 124° C. (with decomposition).

EXAMPLE 25

The process of Example 3 was followed by using 6.3 g of 2-amino-4-methylsulfonyl-N-(4'-chloro-3'-sulfamoylbenzoyl)phenylhydrazine, 35 ml of pyridine and 2.4 g of potassium ethyl xanthate as starting materials to obtain 5 g (73%) of 1-(4'-chloro-3'-sulfamoylbenzoyl)amino-5-methylsulfonylbenzimidazole-2-thione, m.p.: 298°–300° C. after recrystallization from 50% aqueous ethanol.

Analysis (%) for $C_{15}H_{13}ClN_4O_5S_3$:

| | |
|---|---|
| calculated: | C 39.08; H 2.82; N 12.16; Cl 7.69; S 20.87; |
| found: | C 38.90; H 2.70; N 12.12; Cl 7.98; S 20.60. |

Preparation of the starting materials (A) The process of Example 24(A) was followed by using 12.5 g of 4-methylsulfonyl-2-nitrochlorobenzene [prepared as described in: J. Am. Chem. Soc. 75, 642 (1953)], 50 ml of abs. ethanol and 5.3 ml of hydrazine hydrate to give 11 g (92%) of 4-methylsulfonyl-2-nitrophenylhydrazine, m.p.: 188°–190° C.

Analysis (%) for $C_7H_9N_3O_4S$:

| calculated: | C 36.36; H 3.92; N 18.17; S 13.87; |
|---|---|
| found: | C 36.23; H 3.36; N 18.17; S 13.97; |

(B) The process of Example 1(B) was followed by using 11 g of phenylhydrazine derivative prepared according to Example 25(A), 120 ml of dioxane, 2.5 g of anhydrous sodium carbonate dissolved in 47 ml of water and 12 g of 4-chloro-3-sulfamoylbenzoyl chloride dissolved in 95 ml of dioxane as starting materials. Thus, 19.5 g (94%) of 4-methylsulfonyl-2-nitro-N-(4'-chloro-3'-sulfamoylbenzoyl)phenylhydrazine were obtained, m.p.: 279° C. (with decomposition) after recrystallization from acetic acid.

Analysis (%) $C_{13}H_{13}ClN_4O_7S_2$:

| calculated: | C 35.73; H 3.00; N 12.82; Cl 8.11; S 14.67; |
|---|---|
| found: | C 35.75; H 2.90; N 12.49; Cl 7.91; S 14.24. |

(C) The process of Example 1(C) was followed by using 14.8 g of the nitro compound prepared according to Example 25(B), 250 ml of methoxyethanol and 2 g Raney nickel catalyst to yield 14.1 g (99%) of 2-amino-4-methylsulfonyl-N-(4'-chloro-3'-sulfamoylbenzoyl)-phenylhydrazine, m.p.: 200° C. (with decomposition) after recrystallization from ethanol.

Analysis (%) for $C_{14}H_{15}ClN_4O_5S_2$:

| calculated: | C 40.14; H 3.61; N 13.38; Cl 8.46; S 15.31; |
|---|---|
| found: | C 40.51; H 3.77; N 13.65; Cl 8.83; S 15.43. |

EXAMPLE 26

The process of Example 16 was followed by using 1-[4'-chloro-3'-(N-dimethylaminomethylidene)-sulfamoylbenzoyl]amino-5-trifluoromethylbenzimidazole and 80 ml of 2N sodium hydroxide solution as starting materials. After recrystallization of the crude product from a mixture of benzene and acetone (1:1), 14 g (77.7%) of 1-(4'-chloro-3'-sulfamoylbenzoyl)amino-5-trifluoromethylbenzimidazole were obtained, m.p.: 164° C.

Analysis (%) for $C_{15}H_{10}ClF_3N_4O_3S$:

| calculated: | C 43.01; H 2.41; N 13.38; Cl 8.47; |
|---|---|
| found: | C 43.82; H 2.78; N 13.56; Cl 8.11. |

Preparation of the starting materials (A) 64 g of 2-nitro-4-trifluoromethylphenylhydrazine [prepared as described in: J. Org. Chem. 42, 542 (1977)] were heated with 200 ml of 85% formic acid in a water bath for 90 minutes. After cooling down, the yellow solution was poured into 250 ml of water. The crystalline precipitate was filtered by suction, washed with water and dried at 80° C. to yield 72 g (98%) of 2-nitro-4-trifluoromethyl-N-formylphenylhydrazine, m.p.: 152°–153° C.

Analysis (%) for $C_8H_6F_3N_3O_3$:

| calculated: | C 38.56; H 2.43; N 16.86; |
|---|---|
| found: | C 38.38; H 2.48; N 16.98. |

(B) 6 g of 10% palladium-on-carbon catalyst were added to a solution of 65.45 g of nitro compound prepared according to Example 26(A) in 780 ml of abs. ethanol, then the mixture was hydrogenated at room temperature and atmospheric pressure until the hydrogen uptake ceased. After filtering off the catalyst, the filtrate was evaporated to give 55.8 g of 2-amino-4-trifluoromethyl-N-formylphenylhydrazine, m.p.: 121°–122° C.

Analysis (%) for $C_8H_8F_3N_3O$:

| calculated: | C 43.84; H 3.68; N 19.18; |
|---|---|
| found: | C 43.25; H 3.94; N 19.19. |

(C) After boiling 44 g of the phenylhydrazine derivative prepared according to Example 26(B) with 200 ml of 85% formic acid for 5 hours, the red solution obtained was evaporated under reduced pressure. After triturating the residue with 200 ml of water, the crystalline precipitate was filtered by suction, washed with water and dried at 80° C. to yield 40.8 g (88.7%) of 1-formylamino-5-trifluoromethylbenzimidazole, m.p.: 209°–210° C. after recrystallization from a mixture of acetone and water (1:2).

Analysis (%) for $C_9H_6F_3N_3O$:

| calculated: | C 47.17; H 2.64; N 18.34; |
|---|---|
| found: | C 47.69; H 2.59; N 18.51. |

(D) After boiling 15.11 g of the benzimidazole derivative prepared according to Example 26(C) with 68 ml of 2N hydrochloric acid for 5 hours, the solution obtained was made alkaline by adding 2N sodium hydroxide solution. The crystalline precipitate was filtered by suction, washed with water and dried at 80° C. to obtain 11.7 g (88%) of 1-amino-5-trifluoromethylbenzimidazole, m.p.: 140°–142° C.

Analysis (%) for $C_8H_6F_3N_3$:

| calculated: | C 47.76; H 3.00; N 20.89; |
|---|---|
| found: | C 47.82; H 2.94; N 20.64. |

(E) The process of Example 14 was followed by using 8.69 g of the benzimidazole derivative prepared according to Example 26(D), 10 ml of pyridine and 13.35 g of 4-chloro-3-(N-dimethylaminomethylidene)sulfamoylbenzoyl chloride as starting materials. Thus, 20.27 g (100%) of 1-[4'-chloro-3'-(N-dimethylaminomethylidene)sulfamoylbenzoyl]amino-5-trifluoromethylbenzimidazole were obtained, m.p.: 266°–270° C. after recrystallization from methanol.

Analysis (%) for $C_{18}H_{15}ClF_3N_5O_3S$:

| calculated: | C 45.62; H 3.19; N 14.78; S 6.77; |
|---|---|
| found: | C 45.70; H 3.94; N 14.35; S 6.98. |

EXAMPLE 27

The process of Example 16 was followed by using 7.4 g of 1-[4'-chloro-3'-(N-dimethylaminomethylidene)sulfamoylbenzoyl]amino-2-methyl-5-trifluoromethylbenzimidazole and 20 ml of 2N sodium hydroxide solution as starting materials to yield 5.3 g (80.7%) of 1-(4'-chloro-3'-sulfamoylbenzoyl)amino-2-methyl-5-trifluoromethylbenzimidazole, m.p.: 193°–195° C. after recrystallization from a mixture of benzene and acetone (1:1).

Analysis (%) for $C_{16}H_{12}ClF_3N_4O_3S$:

| calculated: | C 44.40; H 2.80; N 12.95; Cl 8.19; |
|---|---|
| found: | C 44.92; H 2.64; N 13.13; Cl 8.36. |

Preparation of the starting materials (A) After boiling 23.3 g of 2-amino-4-trifluoromethyl-N-acetylphenylhydrazine [prepared as described in: J. Org. Chem. 42, 542 (1977)] with 120 ml of acetic acid and 20 ml of acetic anhydride for 6 hours, the orange-red solution obtained was evaporated under reduced pressure and the residue was triturated with water. The separated crystals were filtered by suction, washed with water and dried at 80° C. to yield 23.2 g (90%) of 1-acetylamino-2-methyl-5-trifluoromethylbenzimidazole, m.p.: 214°–216° C. after recrystallization from acetone.

Analysis (%) for $C_{11}H_{10}F_3N_3O$:

| calculated: | C 51.36; H 3.92; N 16.34; |
|---|---|
| found: | C 51.43; H 3.98; N 16.38. |

(B) After boiling 71.14 g of the benzimidazole derivative prepared according to Example 27(A) with 300 ml of 2N hydrochloric acid for 5 hours, the yellow hot solution was clarified by activated carbon and filtered. The filtrate was neutralized to pH 6 by adding 10N sodium hydroxide solution. The snow-white crystalline precipitate was filtered by suction, thoroughly washed with water and dried at 80° C. to give 53.2 g (89.5%) of 1-amino-2-methyl-5-trifluoromethylbenzimidazole, m.p.: 190°–192° C.

Analysis (%) for $C_9H_8F_3N_3$:

| calculated: | C 50.23; H 3.75; N 19.23; |
|---|---|
| found: | C 50.35; H 3.97; N 19.63. |

(C) The process of Example 14 was followed by using 18.02 g of the benzimidazole derivative prepared according to Example 27(B), 25 ml of pyridine and 25.9 g of 4-chloro-3-(N-dimethylaminomethylidene)sulfamoylbenzoyl chloride as starting materials to obtain 34.4 g (84%) of 1-[4'-chloro-3'-(N-dimethylaminomethylidene)sulfamoylbenzoyl]amino-2-methyl-5-trifluoromethylbenzimidazole, m.p.: 300° C.

EXAMPLE 28

The process of Example 16 was followed by using 11.33 g of 1-[4'-chloro-3'-(N-dimethylaminomethylidene)sulfamoylbenzoyl]amino-5-trifluoromethylbenzimidazole-2-thione and 50 ml of 2N sodium hydroxide solution as starting materials. Thus, 7.92 g (77.7%) of 1-(4'-chloro-3'-sulfamoylbenzoyl)amino-5-trifluoromethylbenzimidazole-2-thione were obtained, m.p.: 282°–283° C. (with decomposition) after recrystallization from 50% aqueous ethanol.

Analysis (%) for $C_{15}H_{10}F_3ClN_4O_3S_2$:

| calculated: | C 39.96; H 2.24; N 12.43; Cl 7.86; |
|---|---|
| found: | C 39.06; H 2.12; N 12.20; Cl 7.11. |

Preparation of the starting materials (A) The process of Example 14 was followed by using 8.84 g of 2-nitro-4-trifluoromethylphenylhydrazine, 50 ml of pyridine and 12.36 g of 4-chloro-3-(N-dimethylaminomethylidene)sulfamoylbenzoyl chloride as starting materials to yield 17 g (86%) of 2-nitro-4-trifluoromethyl-N-[4'-chloro-3'-(N-dimethylaminomethylidene)sulfamoylbenzoyl]phenylhydrazine, m.p.: 261°–262° C. (with decomposition) after recrystallization from acetic acid.

Analysis (%) for $C_{17}H_{15}ClF_3N_5O_5S$:

| calculated: | C 41.34; H 3.06; N 14.19; |
|---|---|
| found: | C 41.23; H 3.36; N 14.09. |

(B) The process of Example 2(B) was followed by using 17 g of the nitro compound prepared according to Example 28(A), 1.5 g of 10% palladium-on-carbon catalyst, 100 ml of 96% ethanol and 60 ml of 30% aqueous sodium hypophosphite solution as starting materials. Thus, 11.45 g (72%) of 2-amino-4-trifluoromethyl-N-[4'-chloro-3'-(N-dimethylaminomethylidene)-sulfamoylbenzoyl]phenylhydrazine were obtained, m.p.: 199°–200° C. (with decomposition) after recrystallization from 96% ethanol.

Analysis (%) for $C_{17}H_{17}ClF_3N_5O_3S$:

| calculated: | C 44.01; H 3.69; N 15.10; Cl 7.64; |
|---|---|
| found: | C 43.98; H 3.62; N 14.98; Cl 7.27. |

(C) The process of Example 3 was followed by using 10.4 g of the phenylhydrazine derivative prepared according to Example 28(B), 45 ml of pyridine and 3.6 g of potassium ethyl xanthate as starting materials. Thus, 11.33 g (100%) of 1-[4'-chloro-3'-(N-dimethylaminomethylidene)sulfamoylbenzoyl]amino-5-trifluoromethylbenzimidazole-2-thione were obtained. This product was used without further purification.

EXAMPLE 29

The process of Example 14 was followed by using 5.55 g of 1-amino-2-phenyl-5-trifluoromethylbenzimidazole, 15 ml of pyridine and 6.2 g of 4-chloro-3-(N-dimethylaminomethylidene)sulfamoylbenzoyl chloride as starting materials to obtain 9.7 g of 1-[4'-chloro-3'-(N-dimethylaminomethylidene)sulfamoylbenzoyl]amino-2-phenyl-5-trifluoromethylbenzimidazole which was then hydrolyzed by 50 ml of 2N sodium hydroxide solution as described in Example 16. Thus, 7 g (98%) of 1-(4'-chloro-3'-sulfamoylbenzoyl)amino-2-phenyl-5-trifluoromethylbenzimidazole were obtained, m.p.: 282°–284° C. (with decomposition) after recrystallization from butanol. The compound contained 1 molecule of butanol.

Analysis (%) for $C_{21}H_{14}ClF_3N_4O_3S \cdot C_4H_9OH$:

| calculated: | C 52.76; H 4.25; N 9.84; |
|---|---|
| found: | C 52.35; H 4.37; N 9.66. |

Preparation of the starting materials (A) The process of Example 14 was followed by using 66.5 g of 2-amino-4-trifluoromethyl-N-acetylphenylhydrazine, 70 ml of pyridine and 32.9 ml of benzoyl chloride as starting materials to yield 90 g (93.6%) of 2-benzoylamino-4-trifluoromethyl-N-acetylphenylhydrazine, m.p.: 212°–214° C. after recrystallization from 96% ethanol.

Analysis (%) for $C_{16}H_{14}F_3N_3O_2$:

| calculated: | C 56.97; N 4.18; N 12.46; |
| --- | --- |
| found: | C 57.15; H 4.08; N 12.48. |

(B) After boiling 52.2 g of the phenylhydrazine derivative prepared according to Example 29(A) with 270 ml of glacial acetic acid for 6 hours, the solution obtained was evaporated under reduced pressure and the residue was triturated with water. The crystals were filtered by suction, washed with water and dried at 80° C. to yield 46.3 g (88.5%) of 1-acetylamino-2-phenyl-5-trifluoromethylbenzimidazole, m.p.: 150°–154° C. after recrystallization from 50% aqueous ethanol.

Analysis (%) for $C_{16}H_{12}F_3N_3O$:

| calculated: | C 60.19; H 3.79; N 13.16; |
| --- | --- |
| found: | C 59.98; H 3.74; N 13.04. |

(C) After boiling 45 g of the benzimidazole derivative prepared according to Example 29(B) with a mixture of 100 ml of 96% ethanol and 300 ml of 2N hydrochloric acid for 8 hours, the hot solution was clarified by activated carbon and filtered. After making the filtrate alkaline to pH 10 by adding sodium hydroxide solution, the precipitate was filtered by suction, washed with water and dried at 80° C. to yield 34.1 g (87%) of 1-amino-2-phenyl-5-trifluoromethylbenzimidazole, m.p.: 200°–203° C. after recrystallization from 96% ethanol.

Analysis (%) for $C_{14}H_{10}F_3N_3$:

| calculated: | C 60.65; H 3.64; N 15.16; |
| --- | --- |
| found: | C 60.25; H 3.24; N 15.58. |

EXAMPLE 30

The process of Example 14 was followed by using 9.88 g of 1-amino-2-methylthio-5-trifluoromethylbenzimidazole, 20 ml of pyridine and 12.2 g of 4-chloro-3-(N-dimethylaminomethylidene)sulfamoylbenzoyl chloride as starting materials. The thus obtained 19.4 g (98%) of 1-[4'-chloro-3'-(N-dimethylaminomethylidene)-sulfamoylbenzoyl]amino-2-methylthiobenzimidazole were hydrolyzed by using 100 ml of 2N sodium hydroxide solution as described in Example 16. Thus, 15.45 g (83%) of 1-(4'-chloro-3'-sulfamoylbenzoyl)-amino-2-methylthio-5-trifluoromethylbenzimidazole were obtained, m.p.: 126°–128° C. (with decomposition) after recrystallization from ethyl acetate.

Analysis (%) for $C_{16}H_{12}ClF_3N_4O_3S_2$:

| calculated: | C 41.34; H 2.73; N 10.34; |
| --- | --- |
| found: | C 41.38; H 2.78; N 10.61. |

Preparation of the starting materials (A) After adding 69.96 g of 2-amino-4-trifluoromethyl-N-acetylphenylhydrazine to a solution of 19.07 g of potassium hydroxide in 300 ml of abs. ethanol, 20.5 ml of carbon disulfide were dropped to the mixture under stirring. The red solution obtained was refluxed for 5 hours, the hot solution was clarified by activated carbon and filtered. After adding 370 ml of water and then 70 ml of a mixture of acetic acid and water (1:2) to the filtrate, the crystalline precipitate was filtered by suction, washed with water and dried at 80° C. Thus, 55.5 g (67%) of 1-acetylamino-5-trifluoromethylbenzimidazole-2-thione were obtained, m.p.: 294°–295° C. after recrystallization from 50% of aqueous ethanol.

Analysis (%) for $C_{10}H_8F_3N_3OS$:

| calculated: | C 43.63; H 2.93; N 15.27; |
| --- | --- |
| found: | C 43.52; H 2.95; N 15.40. |

(B) 10 ml of dimethyl sulfate were added to a suspension containing 27.5 g of the benzimidazole derivative prepared according to Example 30(A) in 200 ml of 1N sodium hydroxide solution. At the beginning, the suspension was difficult to stir, however, it was transformed within a few minutes. The mixture was stirred in a hot water bath for 30 minutes, then cooled down. The precipitate was filtered by suction, washed with water and dried at 80° C. to yield 27.2 g (94%) of 1-acetylamino-2-methylthio-5-trifluoromethylbenzimidazole, m.p.: 175°–178° C. after recrystallization from benzene.

Analysis (%) for $C_{11}H_{10}F_3N_3OS$:

| calculated: | C 45.67; H 3.48; N 14.52; |
| --- | --- |
| found: | C 45.36; H 3.76; N 14.27. |

(C) 22.2 g of the benzimidazole derivative prepared according to Example 30(B) were boiled with 80 ml of 2N hydrochloric acid for 6.5 hours, then evaporated to dryness under reduced pressure. The solid residue was strewed into 80 ml of 1N sodium carbonate solution and heated until the bubbling ceased. After cooling down, the crystalline precipitate was filtered by suction, washed with water and dried at 80° C. Thus, 16.85 g (88.5%) of 1-amino-2-methylthio-5-trifluoromethylbenzimidazole were obtained, m.p.: 170°–173° C. after recrystallization from 50% aqueous ethanol.

Analysis (%) for $C_9H_8F_3N_3S$:

| calculated: | C 43.72; H 3.26; N 16.99; |
| --- | --- |
| found: | C 43.65; H 3.17; N 16.64. |

EXAMPLE 31

The process of Example 8 was followed by using 11.25 g of 1-(4'-chloro-3'-sulfamoylbenzoyl)amino-5-trifluoromethylbenzimidazole-2-thione as starting material to obtain 10.8 g (93%) of 1-(4'-chloro-3'-sulfamoylbenzoyl)amino-2-methylthio-5-trifluoromethylbenzimidazole which was in all respects identical with the product prepared in Example 29.

EXAMPLE 32

After dropping 1.46 ml of thionyl chloride to a solution containing 8.2 g of 1-(4'-chloro-3'-sulfamoylbenzoyl)amino-2-methyl-5-carboxybenzimidazole in 50 ml of methanol while stirring, the reaction mixture was refluxed for 5 hours. The clear solution obtained was evaporated to dryness under reduced pressure and the solid residue was triturated with 1N sodium bicarbonate solution. After decanting the solution from the solid product, the residue was recrystallized from a mixture of dioxane and water (1:1). Thus, 6.35 g (75%) of 1-(4'-chloro-3'-sulfamoylbenzoyl)amino-5-methoxycarbonyl-2-methylbenzimidazole were obtained, m.p.: 251°–252° C. (with decomposition).

Analysis (%) for $C_{17}H_{15}ClN_4O_5S$:

| calculated: | C 48.28; H 3.58; N 13.25; Cl 8.39; S 7.58; |
|---|---|
| found: | C 47.98; H 3.38; N 12.95; Cl 8.12; S 7.52. |

Investigation of the saluretic effect in rats

The screening tests were carried out on male LATI CFY rats having an average body-weight of 240 g. The animals were kept on standard rat food and starved for 16 hours before the experiment but they received water ad libitum. For evaluation of the diuretic effect, the method of Lipschitz as modified by Kagawa and Kahn [Arch. Int. Pharmacodyn. 137, 241 (1962)] was used. The results are summarized in Table 1.

Investigation of the saluretic effect on dogs

The compound described in Example 1 was studied also on perineotomized female dogs. The dogs had previously been observed for 2 weeks without any treatment, then subjected to the surgical intervention. For adaptation, starting from the 4th week following the operation, the urinary bladder of the animals was evacuated by a catheter or treated with saline via a gastric tube. During the experiment, the dogs were kept on a standard food and they received water ad libitum. On the days of the experiements, the dogs were fasted and received only 20 ml/kg of water. Sodium in an 7.7 mmol/kg and potassium in an amount of 6.02 mmol/kg were introduced with the food.

On the day of the experiment, the bladder of the animals was evacuated and a blood sample was taken from the leg vein, then a solution of the diuretic and solvent to the controls, respectively were administered in a dose of 10 ml/kg via a gastric tube. The animals were placed separately in metabolic cages. After 7 and 24 hours, respectively the bladder of the animals was catheterized and the urine was collected by washing the metabolic cage. After 24 hours following the catheterization, a blood sample was taken again.

In addition to the discharged volume, the $Na^+$ and $K^+$ content of the urine as well as the glucose and cholesterol level of the serum were determined.

Figure 2:
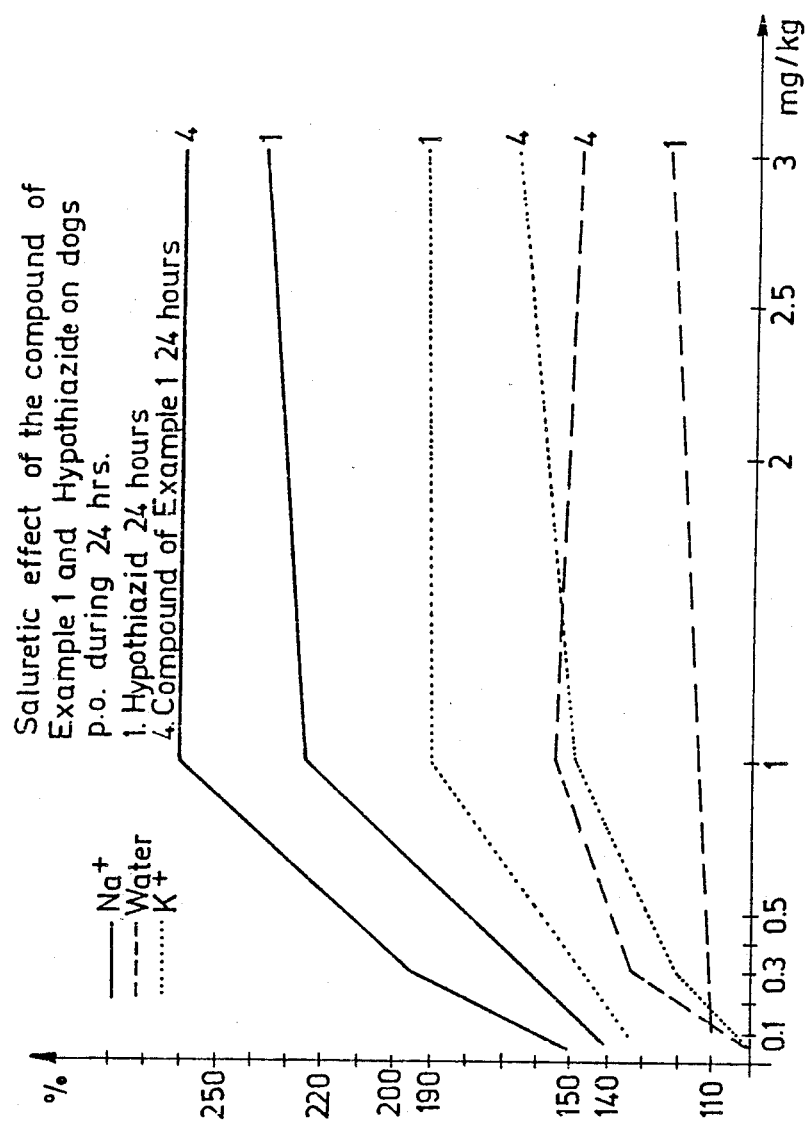

The correlation of the diuretic dose to the water, sodium and potassium discharging effect is shown in FIGS. 1 and 2. FIG. 1 illustrates the results obtained during a 7 hours' period after administering the compound of Example 1 or Furosemide, respectively (since the effect of Hypothiazide is low in this period); FIG. 2 shows; the results of the urinary volume as well as the sodium and potassium content obtained with the product of Example 1 and Hypothiazide, respectively (since the effect of Furosemide is low in the 7 to 24 hours' period).

Investigation of the antihypertensive activity in rats

These investigations were carried but in spontaneously hypertensive (SH) male Okamoto rats. At least one week before starting the experiment, the animals had individually been maintained in cages and received water and semisynthetic rat food ad libitum. In the same time of each day, the blood pressure of each animal was measured and gastric tubing was carried out while immobilizing the animals. Animals with a blood pressure below 170 Hgmm were excluded from the experiment. Based on the daily determined blood pressure values, the animals were divided to experimental groups having a nearly equal average blood pressure and deviation.

At the beginning of the experiment, the animals were given 0.2 ml/100 g of a solution containing the test compound, and 1 ml/100 g of Furosemide solution, respectively. Animal groups treated with physiological saline solution and solvent, respectively were also investigated in each experiment.

Before measuring the blood pressure, the animals were put into a light-insulated sound-proof chamber then immobilized. An inflatable rubber cuff was placed on their tail root (onto the same site in each case) which was connected with a manometer.

The material and diameter of the tail cuff was standardized. The measurement was carried out according to the Riva-Rocci principle. For determining the systolic blood pressure, the palpitation method was used. The heart rate was evaluated by a piezoelectric crystal put onto the rubber ring. The blood pressure measurement of each animal was started by 2 minutes following the immobilization, repeated in every 30 seconds and usually, the values several times repeatedly observed were accepted. The results are summarized in Table 2.

Table 1

Effect of a single oral dose of the compounds according to the invention on water, sodium and potassium diuresis during 24 hours as percentage of the simultaneously measured control values as well as their effect on the Na/K ratio of the urine discharged

| Compound of Example No. | Water | Na | K | Na/K |
|---|---|---|---|---|
| Control | 100 | 100 | 100 | 3.0 |
| 1 | 148 | 152 | 122 | 4.6 |
| 7 | 129 | 133 | 110 | 3.7 |
| 9 | 99 | 105 | 95 | 3.4 |
| 16 | 111 | 117 | 109 | 3.3 |
| 19 | 117 | 121 | 120 | 3.1 |
| 22 | 107 | 99 | 103 | 3.7 |
| 23 | 98 | 105 | 102 | 4.0 |
| 24 | 108 | 104 | 104 | 3.9 |
| 26 | 107 | 108 | 106 | 4.0 |
| 27 | 95 | 94 | 85 | 4.3 |
| 29 | 97 | 101 | 105 | 2.9 |
| 30 | 114 | 106 | 108 | 3.0 |
| 32 | 117 | 121 | 115 | 3.2 |
| Hypothiazide | 124 | 129 | 114 | 3.5 |
| Furosemide | 107 | 106 | 105 | 2.7 |

Table 2

Effect of a single oral dose of the compound of Example 1 or Furosemide, respectively on the systolic blood pressure of SH rats

| Compound and dose | Blood pressure before treatment | Hypotension | | | | |
|---|---|---|---|---|---|---|
| | | 6 hours | | 12 hours | | 24 hours |
| | | following treatment | | | | |
| | mmHg | mmHg | % | mmHg | % | mmHg | % |
| Solvent | 195 | | | | | | |
| Furosemide 100 | 201 | 51 | 25.3 | 39 | 19.4 | 3 | 1.5 |

-continued

| Compound and dose mg/kg | Blood pressure before treatment mmHg | Hypotension | | | | |
|---|---|---|---|---|---|---|
| | | 6 hours following treatment | | 12 hours | | 24 hours |
| | | mmHg | % | mmHg | % | mmHg | % |
| Compound of Example 1 5 mg/kg | 216 | 31 | 14.3 | 45 | 20.1 | 30 | 13.8 |

We claim:

1. A compound of the formula

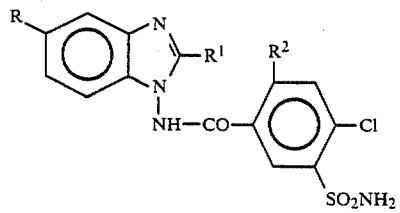

wherein
R is hydrogen atom or a trifluoromethyl, carboxy, $C_{2-5}$alkoxycarbonyl, cyano, benzoyl, sulfamoyl or $C_{1-4}$alkylsulfonyl group;
$R^1$ is hydrogen atom or a linear or branched chain $C_{1-4}$alkyl, $C_{1-4}$alkylthio, $C_{1-4}$alkylsulfonyl, benzylthio, benzylsulfonyl, phenyl, hydroxy or mercapto group; and
$R^2$ is hydrogen or chlorine or a monohydrate or a pharmaceutically acceptable salt thereof.

2. 1-(4'-Chloro-3'-sulfamoylbenzoyl)amino-5-carboxybenzimidazole-2-thione or its monohydrate as defined in claim 1.

3. A pharmaceutical composition, which comprises as active ingredient a compound of the formula

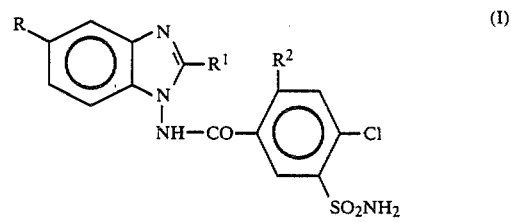

wherein
R is hydrogen atom or a trifluoromethyl, carboxy, $C_{2-5}$alkoxycarbonyl, cyano, benzoyl, sulfamoyl or $C_{1-4}$alkylsulfonyl group;
$R^1$ is hydrogen atom or a linear or branched chain $C_{1-4}$alkyl, $C_{1-4}$alkylthio, $C_{1-4}$alkylsulfonyl, benzylthio, benzylsulfonyl, phenyl, hydroxy or mercapto group; and
$R^2$ is hydrogen or chlorine atom, or a pharmaceutically acceptable salt thereof, in admixture with a pharmaceutically acceptable carrier and/or other excipient.

4. A diuretic and saluretic method of treatment which comprises the step of administering a mammalian subject in need of said treatment, a therapeutically effective amount of the compound of the Formula (I) as defined in claim 1 or a monohydrate or a pharmaceutically acceptable salt thereof.

* * * * *